US008685680B2

(12) United States Patent
Binder et al.

(10) Patent No.: US 8,685,680 B2
(45) Date of Patent: Apr. 1, 2014

(54) METHOD FOR PRODUCING FATS OR OILS

(76) Inventors: Thomas P. Binder, Decatur, IL (US); Scott Bloomer, Decatur, IL (US); Inmok Lee, Decatur, IL (US); Leif Solheim, Decatur, IL (US); Lori E. Wicklund, Argenta, IL (US)

( * ) Notice: Subject to any disclaimer, the term of this patent is extended or adjusted under 35 U.S.C. 154(b) by 160 days.

(21) Appl. No.: 11/432,494

(22) Filed: May 12, 2006

(65) Prior Publication Data

US 2006/0257982 A1 Nov. 16, 2006

Related U.S. Application Data

(60) Provisional application No. 60/680,483, filed on May 13, 2005.

(51) Int. Cl.
*C12P 7/64* (2006.01)
*C12P 7/00* (2006.01)
*C12P 1/00* (2006.01)
*C11B 3/00* (2006.01)

(52) U.S. Cl.
USPC .............. 435/134; 435/132; 435/41; 554/175

(58) Field of Classification Search
USPC .......................................................... 435/134
See application file for complete search history.

(56) References Cited

U.S. PATENT DOCUMENTS 4,103,034 A 7/1978 Ronai et al.
4,153,738 A * 5/1979 Ronai et al. .................. 426/656
4,267,118 A 5/1981 Trueblood et al.
4,798,793 A 1/1989 Eigtved
4,883,684 A 11/1989 Yang
4,940,845 A 7/1990 Hirota et al.
5,124,166 A 6/1992 Jacklin et al.
5,128,251 A 7/1992 Yokomichi et al.
5,149,642 A 9/1992 Mazur et al.
5,166,064 A 11/1992 Usui et al.
5,219,733 A 6/1993 Myojo et al.
5,292,649 A 3/1994 Kosugi et al.
5,399,728 A 3/1995 Cooper
5,578,090 A 11/1996 Bradin
5,713,965 A 2/1998 Foglia et al.
5,773,266 A 6/1998 Bosley et al.
5,874,165 A * 2/1999 Drumheller ................ 428/308.4

(Continued)

FOREIGN PATENT DOCUMENTS

JP 02-203789 A 8/1990
JP 02-203790 A 8/1990

(Continued)

OTHER PUBLICATIONS

Hui, Y. H., ed., "5.6. Deodorization," in: *Bailey's Industrial Oil and Fat Products*, 5th ed., vol. 2, John Wiley and Sons, Inc., New York, NY, pp. 537-540 (1996).

(Continued)

*Primary Examiner* — Sharmila G. Landau
*Assistant Examiner* — Sheridan Macauley
(74) *Attorney, Agent, or Firm* — Scott Bloomer

(57) ABSTRACT

The present invention is directed to improving productivity of an enzymatic method for producing esterified, transesterified or interesterified fats or oils. Specifically, a method that can greatly improve the productivity of enzymatic esterification, transesterification or interesterification by purifying the substrate oil to extend the useful life of the enzyme is disclosed.

19 Claims, 2 Drawing Sheets

(56) References Cited

U.S. PATENT DOCUMENTS

| | | | | |
|---|---|---|---|---|
| 6,004,611 | A | 12/1999 | Gotoh et al. | |
| 6,172,248 | B1 | 1/2001 | Copeland et al. | |
| 6,398,707 | B1 | 6/2002 | Wu et al. | |
| 6,511,690 | B1 | 1/2003 | Tysinger et al. | |
| 2003/0054509 | A1 * | 3/2003 | Lee et al. | 435/134 |
| 2005/0014237 | A1 | 1/2005 | Lee | |
| 2005/0019316 | A1 | 1/2005 | Ten Brink et al. | |

FOREIGN PATENT DOCUMENTS

| | | | |
|---|---|---|---|
| JP | 08-140689 | A | 6/1996 |
| JP | 11-103884 | A | 4/1999 |
| JP | 2003-310290 | A | 11/2003 |

OTHER PUBLICATIONS

Hui, Y. H., ed., "6. Deodorization," in: *Bailey's Industrial Oil and Fat Products*, 5th ed., vol. 4, John Wiley and Sons, Inc., New York, NY, pp. 339-390 (1996).

Bjurlin, M., et al., "Composition and Activity of Commercial Triacylglycerol Acylhydrolase Preparations," *J. Amer. Oil Chem. Soc*. 78:153-160, American Oil Chemists' Society (2001).

Brekke, O.L., "Deodorization," in: *Handbook of Soy Oil Processing and Utilization*, Erickson, D. R., et al., eds., American Soybean Association and the American Oil Chemists' Society Press, St. Louis, MO, pp. 155-191 (1980).

Diks, Rob M.M., "Lipase stability in oil," *Lipid Technology*, 14:10-14, Barnes & Associates (2002).

Egbert, W.R., "Isolated Soy Protein: Technology, Properties, and Applications," in: *Soybeans as Functional Foods and Ingredients*, KeShun L., ed., AOCS Press, Champaign, IL, pp. 134-163 (2004).

Ferreira-Dias, S. et al. "Recovery of the activity of an immobilized lipase after its use in fat transesterification," *Prog. Biotechnol*. 15: 435-440, Elsevier Science B.V. (1998).

Franzen, K.L. and Kinsella, J.E., "Parameters Affecting the Binding of Volatile Flavor Compounds in Model Food Systems. I Proteins," *J. Agric. Food Chem*. 22:675-678, American Chemical Society (1974).

Gardner, H.W., "Lipid Hydroperoxide Reactivity with Proteins and Amino Acids: A Review," *J. Agric. Food Chem*. 17:220-229, American Chemical Society (1979).

Gray, J.I., "Measurement of Lipid Oxidation: A Review," *J. Amer. Oil Chem. Soc*. 55.539-546, American Oil Chemists' Society Press (1978).

Huang, F.-C. and Ju, Y.-H., "Interesterification of palm midfraction and stearic acid with *Rhizopus arrhizus* lipase immobilized on polypropylene," *Journal of the Chinese Institute of Chemical Engineers* 28:73-78 (1997).

Jung; H.J. and Bauer, W., "Determination of Process. Parameters and Modeling of Lipase-Catalyzed Transesterification in a Fixed Bed Reactor," *Chem. Eng. Technol*., 15:341-348, VCH Verlagsgesellschaft mbH (1992).

Macrae, A.R., "Lipase-Catalyze Interesterification of Oils and Fats," *J. Am. Oil Chem. Soc*. 60:243A-246A, American Oil Chemists' Society Press (1983).

Matsushita, S., "Specific Interactions of Linoleic Acid Hydroperoxidases and Their Secondary Degraded Products with Enzyme Proteins," *J. Agric. Food Chem*. 23:150-154, American Chemical Society (1975).

Merolli, A., et at, "Medium-chain lipids: new sources, uses," *INFORM* 8:597-603, American Oil Chemists' Society Press (1997).

Nezu, T., et al., "The Effect of Lipids Oxidation on the Activity of Interesterification of Triglyceride by Immobilized Lipase," in: *Dev. Food Eng., 6th Proc. Int. Congr. Eng. Food*, Blackie Academic & Professional, London, GB, pp. 591-593 (1994).

Ohta, Y., et al., "Inhibition and Inactivation of Lipase by Fat Peroxidase in the Course of Batch and Continuous Glycerolyses of Fat by Lipase," *Agric. Biol. Chem*. 53:1885-1890, Agricultural Chemical Society of Japan (1989).

Pirozzi, D., "Improvement of lipase stability in the presence of commercial triglycerides," *Eur. J. Lipid Sci. Technol*. 105:608-613, Wiley-VCH Verlag GmbH & Co. (2003).

Rousseau, D. and Marangoni, A.G., "Chemical Interesterification of Food Lipids: Theory and Practice," in: *Food Lipids Chemistry, Nutrition, and Biotechnology, Second Edition, Revised and Expanded*, Akoh, C.C. and Min, D.B., eds., Marcel Dekker, Inc., New York, NY, pp. 301-333 (2002).

Soares, C.M.F:, et al., "Selection of Stabilizing Additive for Lipase Immobilization on Controlled Pore Silica by Factorial Design," *Appl. Biochem. Biotechnol*. 91-93:703-718 (2001).

Van der Padt, A., et al., "Synthesis of Triacylglycerols. The crucial role of water activity control," *Prog. Biotechnol, Biocatalysis in Non-Conventional Media* 8:557-562, Elsevier Science Publishers B.V. (1992).

Wang, Y. and Gordon, M.H., "Effect of Lipid Oxidation Products on the Transesterification Activity of an Immobilized Lipase," *J. Agric. Food Chem*., 39:1693-1695, American Chemical Society (1991).

Xu, X., "Modification of Oils and Fats by Lipase-Catalyzed Interesterification: Aspects of Process Engineering," in: *Enzymes in: Lipid Modification*, Wiley-VCH Verlag GmbH, Berlin, DE, pp. 190-215 (2000).

Zhang, H., et al., "Production of Margarine Fats by Enzymatic Interesterification with Silica-Granulated *Thermomyces lanuginosa* Lipase in a Large-Scale Study," *J. Am. Oil Chem. Soc*. 78: 57-64, American Oil Chemists Society Press (2001).

Unverified partial translation of JP 02-203789 A2, 2 pages (listed on accompanying PTO/SB/08A as document FP1).

Unverified translation of JP 02-203790 A2, 8 pages (listed on accompanying PTO/SB/08A as document FP2).

Unverified translation of JP 08-140689 A2, 8 pages (listed on accompanying PTO/SB/08A as document FP3).

Unverified partial translation of JP 11-103884, 3 pages. (listed on accompanying PTO/SB/08A as document FP4).

Unverified partial translation of JP 2003-310290, 3 pages (listed on accompanying PTO/SB/08A as document FP5).

U.S. Appl. No. 11/598,106, inventors Bao, W., et al., filed Nov. 13, 2006.

Modic P et al; Absorption of water, fat, bouillon and water-fat systems by textured vegetable proteins, Technologija Mesa, vol. 14, pp. 322-325, Journal Article 1973 Yugoslavia.

Kajimoto, G., Loss ratios of amino acid by oxidative rancid oil and thermally oxidized oil, (Abstract), J. Agric. Chem. Soc. Japan, 1973, p. 515-522, vol. 47, Japan.

Camire, M. E., Chemical and Nutritional Changes in Food During Extrusion; in Extruders in Food Applications, Ch. 7, p. 134, (2000) M. Riaz, ed. Technomic Publ. Co., Lancaster, PA).

Camire, M., J. Amer. Oil Chem. Soc. 68, 200-205, 1991, "Protein Functionality Modification by Extrusion Cooking".

O'Neill, Inform 1990, 1, 215-226, Flavor perception and binding.

"Textured Vegetable Protein" Wikipedia, accessed Apr. 10, 2012.

TVP Processing line image; http://images.tradekool.com/108967100/Textured-Soy-Protein-vegetable-Protein-Processing-Line.jpg, Aug. 24, 2012.

* cited by examiner

Figure 1. Effect of arginine on enzyme stability
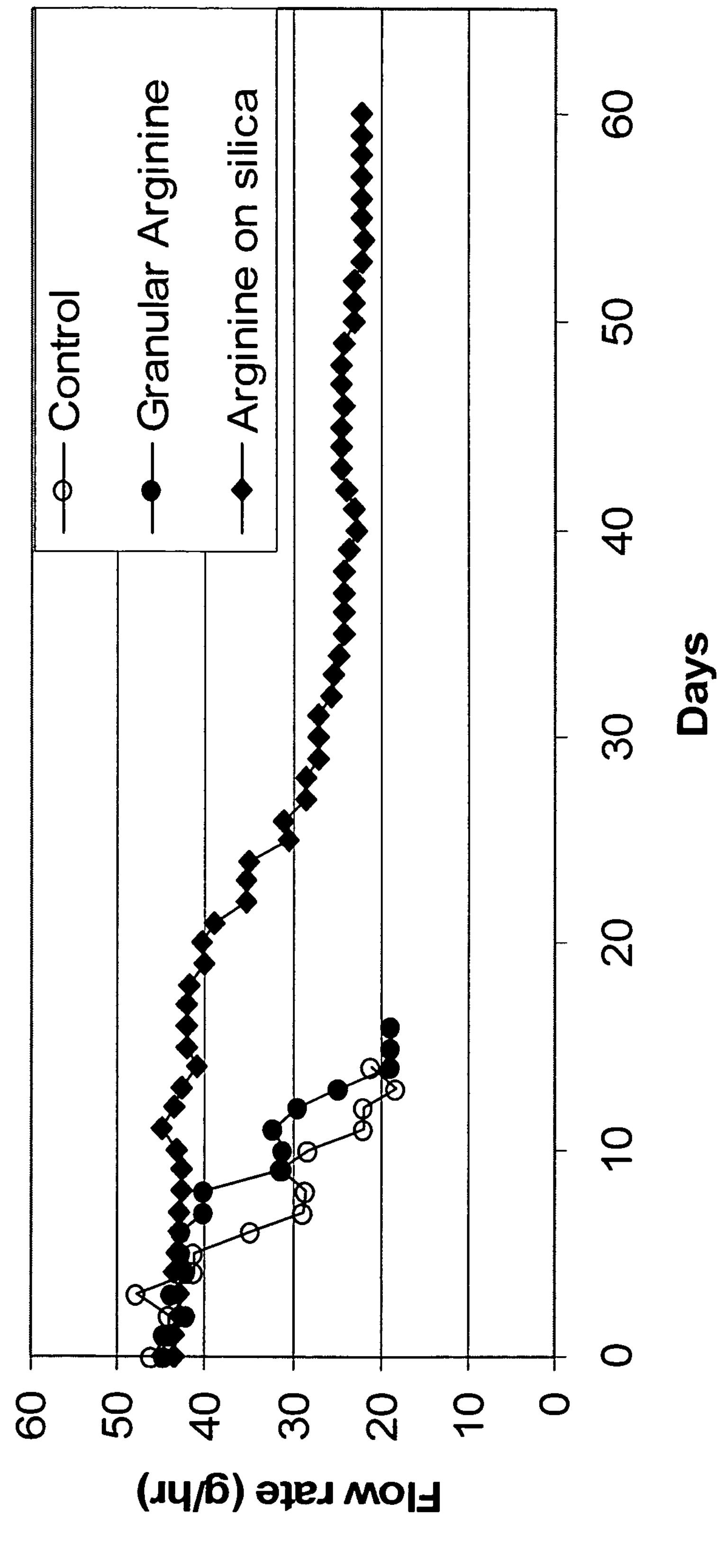

Figure 2. Effect of amino acids on enzyme stability
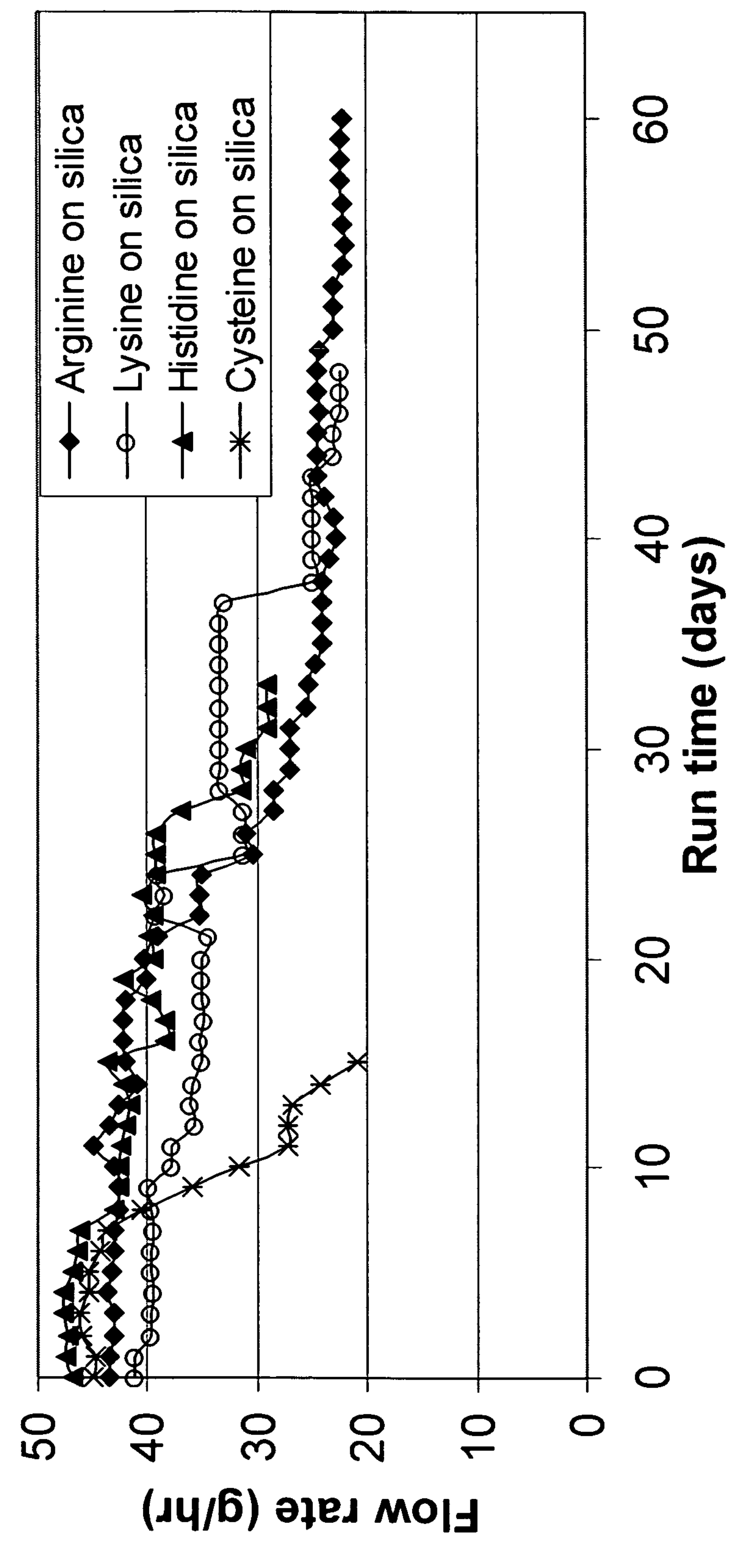

METHOD FOR PRODUCING FATS OR OILS

CROSS REFERENCE TO RELATED APPLICATIONS

This application claims the benefit of U.S. Provisional Application No. 60/680,483, filed May 13, 2005, which is incorporated by reference herein in its entirety.

BACKGROUND OF THE INVENTION

1. Field of the Invention

The present approach relates to methods for producing fats and oils. Specifically, the present approach pertains to prolonging the enzymatic activity of an enzyme used for transesterification or esterification of a substrate for the production of fats and oils by purification of the substrate prior to transesterification or esterification.

2. Related Art

Lipases (triacylglycerol acylhydrolases, EC 3.1.1.3) are able to catalyze a variety of reactions. Such enzymes are commercially available from a broad range of manufacturers and organisms, and are useful in catalyzing reactions with commodity oils and fats. See, e.g., Xu, X., "Modification of oils and fats by lipase-catalyzed interesterification: Aspects of process engineering," in *Enzymes in Lipid Modification,* 190-215 (Bornscheuer, U. T., ed., Wiley-VCH Verlag GmbH, Weinheim, Germany, 2000). Lipases are useful to hydrolyze glycerides such as triacylglycerols and phosphatides. They are also useful in the synthesis of esters from industrial fatty acids and alcohols. In addition, lipases are useful for alcoholysis (exchanging alcohols bound to esters) for products such as biodiesel and partial glycerides. Lipases can also be used to catalyze acyl-exchange reactions such as interesterification (also known as transesterification) of mixed ester substrates to create unique blends of triacylglycerols with desired functional characteristics.

Biocatalysts such as lipases are also attractive due to their use under mild operating conditions and their high degrees of selectivity. Biocatalysts also offer synthetic routes which avoid the need for environmentally harmful chemicals.

Lipases are further useful for the manufacture of specialty glycerides. For example, 1,3-specific lipases are useful in the manufacture of 1,3-diglycerides, as described, for example, in U.S. Pat. No. 6,004,611.

The transesterification reaction has also become an important solution to a recently identified threat to human health: trans fatty acids. These trans fatty acids were long desired for their functional characteristics in food use and have been produced on commodity scale by partial hydrogenation of vegetable oils. Thus, they have been readily available and relatively inexpensive for decades. Currently, suppliers of food products are seeking fats to replace partially hydrogenated vegetable oil, preferably at comparable prices or lower. Transesterification of properly selected fats and oils can provide fats to replace partially hydrogenated vegetable oil. If such fats are produced by transesterification of fats and oils free from trans fatty acids, trans fatty acids will be substantially absent from the transesterified fat. Proper selection of fatty acid compositions of starting fats and oils will provide proper functionality in the transesterified replacement fats for partially hydrogenated oil advantageously synthesized by lipase-catalyzed interesterification.

The stability of biocatalysts such as lipases is most conveniently expressed in terms of half-life, which is the time after which the initial catalyst activity has decreased to half the original value. Diks, Rob M. M., "Lipase stability in oil," *Lipid Technology,* 14(1): 10-14 (2002). Another way to express enzyme stability is the productivity of the enzyme, which is measured by the amount of the product per unit enzyme (g oil produced/g enzyme), during the first half-life. Typical lipase half-lives in interesterification reactions are seven days. See, e.g., Huang, Fang-Cheng and Ju, Yi-Hsu, "Interesterification of palm midfraction and stearic acid with *Rhizopus arrhizus* lipase immobilized on polypropylene," *Journal of the Chinese Institute of Chemical Engineers,* 28(2): 73-78 (1997); Van der Padt, A. et al., "Synthesis of triacylglycerols. The crucial role of water activity control," *Progress in Biotechnology,* 8 (Biocatalysis in Non-Conventional Media): 557-62 (1992). Half-lives vary greatly depending on the lipases themselves.

However, half-lives also vary depending on the quality of the substrates. When biocatalysts such as enzymes are used, components in the substrate mixture may diminish the effective lifetime of the catalyst. In continuous operations, the ratio of substrate processed to enzyme is very large, so minor components of oil can have a cumulative deleterious effect on enzyme activity. Several oxidation compounds in oil, such as hydroperoxides and secondary oxidation products (e.g., aldehydes or ketones), may cause significant lipase inactivation in oils. See, e.g., Pirozzi, Domenico, "Improvement of lipase stability in the presence of commercial triglycerides," *European Journal of Lipid Science and Technology* 105(10): 608-613 (2003); Gray, J. I., "Measurement of Lipid Oxidation: A Review," *J. Amer. Oil Chem. Soc.* 55: 539-546 (1978); U.S. Patent Application Publication No. 2005/0014237 A1, and publications cited therein. Oxidation products include oxidative species that initiate self-propagated radical reaction pathways, or other reactive oxygen species (such as peroxides, ozone, superoxide, etc.). These and other constituents which cause or arise from fat or oil degradation can result in enzyme degradation. The presence of water and other substances can also strongly influence the activity of lipases used in transesterification. See, e.g., Jung, H. J. and Bauer, W., "Determination of process parameters and modeling of lipase-catalyzed transesterification in a fixed bed reactor," *Chemical Engineering & Technology,* 15(5): 341-8 (1992). Some metal ions ($Mg^{2+}$ and $Fe^{2+}$) have also been cited as inhibitors for some lipases. However, the processes and causative factors by which lipases become inactive are not completely understood.

It has been observed that using different batches of the same feedstock in a lipase-catalyzed oil gave wide variations in lipase half-life. Diks, Rob M. M., "Lipase stability in oil," *Lipid Technology,* 14(1): 10-14 (2002). No relationship was found between lipase half-life and the oil's PV or the para-anisidine value (PAV). In addition, no correlation between metal levels (Fe and Cu), polymerized glycerides, or phospholipids and lipase half-life could be established.

An investigation into the cause of loss of activity of immobilized lipase in the acidolysis of high oleic sunflower oil with stearic acid determined that oxidation products increased the rate of deactivation, but removal of oxidation products from the oils prevented activity loss. Nezu, T. et al., "The effect of lipids oxidation on the activity of interesterification of triglyceride by immobilized lipase," in Dev. Food Eng., 6th Proc. Int. Congr. Eng. Food, 591-3 (Yano, T. et al., eds., Blackie, Glasgow, 1994). Immobilized lipases incubated with 2-unsaturated aldehydes (typically formed as secondary oxidation products in the oxidative breakdown of oils) lost their catalytic activity. Linoleic acid hydroperoxides at levels of PV>5 meq/kg causes loss of lipase activity, and the rate of enzyme inactivation increases as PV increased; the mechanism of enzyme inactivation was the generation of free radicals in the enzyme as the peroxides decomposed. Wang, Y. and Gordon, M. H., "Effect of lipid oxidation products on the transesterification activity of an immobilized lipase," *Journal of Agricultural and Food Chemistry,* 39(9): 1693-5 (1991). When oxidized lipids were separated from a sample of palm oil and fractionated, it was demonstrated that fractions exhibiting high degrees of inactivation could be isolated, but the inhibitory compounds were not identified. Id.

Rapid lipase activity decrease during continuous lipase catalyzed reactions is common. See, e.g., Ferreira-Dias, S. et al. "Recovery of the activity of an immobilized lipase after its use in fat transesterification," *Progress in Biotechnology,* 15 (Stability and Stabilization of Biocatalysis): 435-440 (1998); Diks, Rob M. M., "Lipase stability in oil," *Lipid Technology,* 14(1):10-14 (2002).

Several methods have been tried to eliminate loss of activity or to recover activity from inactivated lipase.

a) Recovery of lipase activity lost in transesterification reactions was carried out by washing the lipase preparation with hexane and adjusting the water activity of the preparation to 0.22. Ferreira-Dias, S. et al. "Recovery of the activity of an immobilized lipase after its use in fat transesterification," *Progress in Biotechnology,* 15 (Stability and Stabilization of Biocatalysis): 435-440 (1998). Although the mechanism was unknown, this type of activity recovery is consistent with activity loss caused by accumulation of inhibitory compounds such as lipid oxidation products. Id.

b) Reducing the water activity of a transesterification substrate (crude palm oil/degummed rapeseed oil) from 280 ppm to 60 ppm was accompanied by an increase of immobilized lipase half-life from 10 hours to 100 hours. Huang, Fang-Cheng and Ju, Yi-Hsu, "Interesterification of palm midfraction and stearic acid with *Rhizopus arrhizus* lipase immobilized on polypropylene," *Journal of the Chinese Institute of Chemical Engineers,* 28(2):73-78 (1997).

c) Lipase half life has been increased by immobilizing certain compositions with lipase. For example, the half life of lipase immobilized on controlled pore silica increased five-fold when PEG-1500 was co-immobilized with the lipase. Soares, C. M. F. et al., "Selection of stabilizing additive for lipase immobilization on controlled pore silica by factorial design," *Applied Biochemistry and Biotechnology,* 91-93 (Symposium on Biotechnology for Fuels and Chemicals, 2000):703-718 (2001).

d) JP 11-103884 described the addition of small amounts (0.01-5 wt %) of phospholipids to an immobilized *Alcaligenes* lipase caused a ten-fold increase in lipase half life.

e) Others have prolonged lipase half-life via pre-treatment of the substrate oil. JP 08-140689 A2 describes the use of Duolite A-7 ion exchange resin to treat a blend of palm oil with ethyl stearate prior to interesterification using and immobilized *Rhizopus* lipase to increase the half life from 3 days to 8 days. Duolite A-7 is an anion exchange resin containing amino groups. JP 08-140689 A2 also describes pre-treatment of substrate oils with proteins or peptides containing a large number of basic amino acid residues such as histone, protamine, lysozyme or polylysine. JP 08-140689 A2 states that amino groups are believed to react with aldehydes or ketones (secondary oxidation products) to form a Schiff base; and that such secondary oxidation products are believed to be a factor in lipase inactivation.

f) JP 02-203789 A2 describes extending the half life of immobilized lipase by pre-treatment of the substrate with an alkaline substance. When an equal mixture of rapeseed oil and palm olein was interesterified on a column of lipase immobilized on Celite 535, the half life of the lipase was 18 hours. When the substrate was mixed with a solution of potassium hydroxide (5 mL/kg substrate) the half life of the enzyme activity was 96 h. An alternative approach is to treat celite with sodium hydroxide and mix this into the same substrate mixture. Using this approach, lipase half life was extended to 33 hours. JP 02 203790 A2.

g) It has been demonstrated that, Novozyme 435 is more affected by secondary oxidation products than by hydroperoxides (Pirozzi, Domenico, "Improvement of lipase stability in the presence of commercial triglycerides," *European Journal of Lipid Science and Technology* 105(10):608-613 (2003)). With this lipase, it has been shown that lipase sulphydryl groups interact with two secondary oxidation product aldehydes, 4-hydroxynonenal (4-HNE) and malondialdehyde (MDA). By neutralizing 4-HNE and MDA in oil with albumin, enzyme stability was increased.

h) U.S. Patent Application No. 2003/0054509 describes the use of unmodified purification media (e.g., silica gel) to increase enzymatic half-life. U.S. Patent Application No. 2005/0014237 describes the use of deodorization processes to increase enzymatic half-life.

Hence, there is a long-felt need in the art of enzymatic catalysis for solutions to this activity loss. See also Diks, Rob M. M., "Lipase stability in oil," *Lipid Technology,* 14(1):10-14 (2002); Wang, Y. and Gordon, M. H., "Effect of lipid oxidation products on the transesterification activity of an immobilized lipase," *Journal of Agricultural and Food Chemistry,* 39(9):1693-5 (1991). The time period over which lipase retains its enzymatic activity is an important cost consideration in lipase-catalyzed interesterification. The loss of effective enzyme activity is detrimental to industrial processing due to the cost of replacement enzyme and production time needed to change enzymes, switch columns, and stabilize a new column. Thus, the extension of enzyme half-life is extremely critical for the successful commercialization of enzymatic interesterification. This long-felt need is a primary barrier to the expansion of enzyme catalyzed reactions for production of commodity or "bulk" chemicals.

Although most of the mechanisms of lipase inactivation and its prevention are poorly understood at present, the present approach describes an effective solution to preventing lipase degradation and increasing its productivity and half-life.

SUMMARY OF THE INVENTION

Embodiments of the invention are directed to various methods for producing fats or oils, by contacting an initial substrate comprising one or more glycerides with one or more types of purification media to generate a purified substrate, and contacting the purified substrate with lipase to effect esterification, interesterification or transesterification creating the fats or oils. In the various embodiments of the invention, the purification medium or media can be one or more of amino acids, peptides, polypeptides, or proteins. The amino acids, peptides, polypeptides, or proteins may be coated on a support carrier, thereby forming a purification medium or media used in the methods of the invention.

In an embodiment of the invention, vegetable protein is used as a purification medium. Thus, an embodiment of the invention is directed to a method for producing fats or oils comprising: (a) contacting an initial substrate comprising one or more glycerides with one or more types of vegetable protein to generate a purified substrate; and (b) contacting the purified substrate with lipase to effect esterification, interesterification or transesterification creating the fats or oils. In various embodiments of the invention, the vegetable protein can be a soy protein, or a textured vegetable protein such as a textured soy protein.

In another embodiment of the invention, one or more amino acids are coated on the one or more types of purification media. Thus, an embodiment of the invention is directed to a method for producing fats or oils comprising: (a) contacting an initial substrate comprising one or more glycerides with one or more types of purification media to generate a purified substrate; and (b) contacting the purified substrate with lipase to effect esterification, interesterification or transesterification creating the fats or oils; wherein one or more amino acids are coated on the one or more types of purification media. In various embodiments of the invention, the one or more amino acids can be any of arginine, lysine, histidine and/or cysteine.

In yet another embodiment of the invention, one or more peptides, polypeptides, and/or proteins ("protein material") are coated on the one or more types of purification media. Thus, an embodiment of the invention is directed to a method for producing fats or oils comprising: (a) contacting an initial substrate comprising one or more glycerides with one or more types of purification media to generate a purified substrate; and (b) contacting the purified substrate with lipase to effect esterification, interesterification or transesterification creating the fats or oils; wherein one or more peptides, polypeptides, or proteins (one or more "protein materials") are coated on the one or more types of purification media. The enzymatic activity half-life of the lipase can be more than about 2.5 times greater than the enzymatic activity half-life resulting from contacting the lipase with the initial substrate.

In still yet another embodiment, the invention is directed to use of a protein as a purification medium. Thus, an embodiment of the invention is directed to a method for producing fats or oils comprising: (a) contacting an initial substrate comprising one or more glycerides with one or more proteins to generate a purified substrate; and (b) contacting the purified substrate with lipase to effect esterification, interesterification or transesterification creating the fats or oils. The enzymatic activity half-life of the lipase can be more than about 2.5 times greater than the enzymatic activity half-life resulting from contacting the lipase with the initial substrate.

In still yet another embodiment, the invention is directed to use of a textured protein as a purification medium. Thus, an embodiment of the invention is directed to a method for producing fats or oils comprising: (a) contacting an initial substrate comprising one or more glycerides with one or more types of textured protein to generate a purified substrate; and (b) contacting the purified substrate with lipase to effect esterification, interesterification or transesterification creating the fats or oils.

In various embodiments of the invention, the methods for producing the fats or oils can also include (c) monitoring enzymatic activity by measuring one or more physical properties of the fats or oils after having contacted the lipase; (d) adjusting the duration of time for which the purified substrate contacts the lipase, or adjusting the temperature of the initial substrate, the purified substrate, the one or more types of purification media or the lipase in response to a change in the enzymatic activity to produce fats or oils having a substantially uniform increased proportion of esterification, interesterification, or transesterification relative to the initial substrate; and/or (e) adjusting the amount and type of the one or more types of purification media in response to changes in the physical properties of the fats or oils to increase enzymatic productivity of the lipase. The one or more physical properties can include the Mettler dropping point temperature of the fats or oils and/or the solid fat content profile of the fats or oils.

In the inventive methods, the initial substrate can also include any of free fatty acids, monohydroxyl alcohols, polyhydroxyl alcohols, esters and combinations thereof.

The one or more glycerides used in the inventive methods can be any of i) butterfat, cocoa butter, cocoa butter substitutes, illipe fat, kokum butter, milk fat, mowrah fat, phulwara butter, sal fat, shea fat, borneo tallow, lard, lanolin, beef tallow, mutton tallow, tallow, animal fat, canola oil, castor oil, coconut oil, coriander oil, corn oil, cottonseed oil, hazelnut oil, hempseed oil, jatropha oil, linseed oil, mango kernel oil, meadowfoam oil, mustard oil, neat's foot oil, olive oil, palm oil, palm kernel oil, peanut oil, rapeseed oil, rice bran oil, safflower oil, sasanqua oil, shea butter, soybean oil, sunflower seed oil, tall oil, tsubaki oil, vegetable oils, marine oils which can be converted into plastic fats, marine oils which can be converted into solid fats, menhaden oil, candlefish oil, cod-liver oil, orange roughy oil, pile herd oil, sardine oil, whale oils, herring oils, 1,3-dipalmitoyl-2-monooleine (POP), 1(3)-palmitoyl-3(1)-stearoyl-2-monooleine (POSt), 1,3-distearoyl-2-monooleine (StOSt), triglyceride, diglyceride, monoglyceride, behenic acid triglyceride, trioleine, tripalmitine, tristearine, palm olein, palm stearin, palm kernel olein, palm kernel stearin, triglycerides of medium chain fatty acids, or combinations thereof; ii) processed partially hydrogenated oils of (i); iii) processed fully hydrogenated oils of (i); or iv) fractionated oils of (i).

The initial substrate used in the inventive methods can also include esters. The esters can be any of wax esters, alkyl esters, methyl esters, ethyl esters, isopropyl esters, octadecyl esters, aryl esters, propylene glycol esters, ethylene glycol esters, 1,2-propanediol esters, 1,3-propanediol esters, and combinations thereof. The esters can be formed from the esterification or transesterification of monohydroxyl alcohols or polyhydroxyl alcohols. The monohydroxyl alcohols or the polyhydroxyl alcohols can be primary, secondary or tertiary alcohols of annular, straight or branched chain compounds. The monohydroxyl alcohols can be any of methyl alcohol, isopropyl alcohol, allyl alcohol, ethanol, propanol, n-butanol, iso-butanol, sec-butanol, tert-butanol, n-pentanol, iso-pentanol, n-hexanol or octadecyl alcohol. The polyhydroxyl alcohols can be any of glycerol, propylene glycol, ethylene glycol, 1,2-propanediol or 1,3-propanediol.

The initial substrate used in the inventive methods can also have primary, secondary or tertiary monohydroxyl alcohols of annular, straight or branched chain compounds. The monohydroxyl alcohols can be any of methyl alcohol, isopropyl alcohol, allyl alcohol, ethanol, propanol, n-butanol, iso-butanol, sec-butanol, tert-butanol, n-pentanol, iso-pentanol, n-hexanol or octadecyl alcohol.

The initial substrate used in the inventive methods can also have primary, secondary or tertiary polyhydroxyl alcohols of annular, straight or branched chain compounds. The polyhydroxyl alcohols can be any of glycerol, propylene glycol, ethylene glycol, 1,2-propanediol or 1,3-propanediol.

The initial substrate used in the inventive methods can also have one or more fatty acids which are saturated, unsaturated or polyunsaturated. The one or more fatty acids can have carbon chains from about 4 to about 22 carbons long. The fatty acids can be any of palmitic acid, stearic acid, oleic acid, linoleic acid, linolenic acid, arachidonic acid, erucic acid, caproic acid, caprylic acid, capric acid, lauric acid, myristic acid, eicosapentaenoic acid (EPA), docosahexaenoic acid (DHA), 5-eicosenoic acid, butyric acid, γ-linolenic acid or conjugated linoleic acid.

In embodiments using the inventive methods, the one or more types of purification media and the lipase are packed in one or more columns. The columns can be jacketed columns in which the temperature of the initial substrate, the purified substrate, the one or more types of purification media or the lipase is regulated.

In other embodiments using the inventive methods, the purified substrate can be prepared by mixing the initial substrate with the one or more types of purification media in a tank for a batch slurry purification reaction or mixing the initial substrate in a series of tanks for a series of batch slurry purification reactions. The purified substrate can be separated from the one or more types of purification media via filtration, centrifugation or concentration prior to reacting the purified substrate with the lipase. The purified substrate can then be mixed with the lipase in a tank for a batch slurry reaction, or flowing the purified substrate through a column containing the lipase.

In yet other embodiments of the methods of the invention, a bed of the one or more types of purification media is placed upon a bed of the lipase within a column. The column can be a jacketed column in which the temperature of the initial substrate, the purified substrate, the one or more types of purification media or the lipase is regulated.

The lipase used in the methods of the invention can be obtained from a cultured eukaryotic or prokaryotic cell line. The lipase can be a 1,3-selective lipase or a non-selective lipase. The fats or oils produced can be 1,3-diglycerides.

In embodiments of the invention, the one or more glycerides used in the methods of the invention can be partially hydrogenated soybean oil, partially hydrogenated corn oil, partially hydrogenated cottonseed oil, fully hydrogenated soybean oil, fully hydrogenated corn oil, and/or fully hydrogenated cottonseed oil.

In other embodiments of the invention, the one or more glycerides used in the methods of the invention can be partially hydrogenated palm oil, partially hydrogenated palm kernel oil, fully hydrogenated palm oil, fully hydrogenated palm kernel oil, fractionated palm oil, fractionated palm kernel oil, fractionated partially hydrogenated palm oil, and/or fractionated partially hydrogenated palm kernel oil.

BRIEF DESCRIPTION OF THE FIGURES

FIG. 1 shows the adjustment of pumping rate as a function of run time for lipase exposed to untreated substrate (open circles), substrate treated with granular arginine (closed circles), or substrate treated with arginine-coated silica (closed diamonds).

FIG. 2 shows the adjustment of pumping rate as a function of run time for lipase exposed to substrate treated with arginine-coated silica (closed diamonds), lysine-coated silica (open circles), histidine-coated silica (closed triangles), and cysteine-coated silica (stars "*").

DETAILED DESCRIPTION OF THE INVENTION

The present approach relates to increasing the productivity or enzymatic half-life of enzymes that catalyze esterification, interesterification or transesterification. In particular, the present approach relates to the removal from an initial substrate of constituents which cause lipase degradation. Such constituents may cause or arise from fat or oil degradation, from substrate handling or processing, or from other causes. Such constituents can be removed by treatment of the initial substrate with a purification medium prior to contacting the lipase. The purification medium can be one or more amino acids, peptides, polypeptides or proteins, which are kept separate from the enzyme. The amino acids, peptides, polypeptides or proteins can be coated on a solid support carrier via absorption, adsorption, covalent bonds, ionic bonds or hydrogen bonds.

Treatment of substrates with amino acids is advantageous over use of conventional amino-group-containing substances, such as those described in JP 08-140689 A2. The advantage of using amino acids is due to the greater steric freedom of free amino acids. Amino-groups of conventional amino-group-containing substances are bound and less readily available to react with secondary oxidation products.

The present approach also relates to testing amino acids for their ability to be used to purify initial substrate and increase the half-life of enzymes. An amino acid that is crucial to inactivation of an enzyme can be specifically selected by experiments for the protection of an enzyme. For example, cysteine can be used for the enzyme whose inactivation is related to the oxidation of the sulfhydryl group.

Denaturation of the side chains of enzymes, especially at the active sites, is believed to be a cause of the loss of enzyme activity. The denaturation can be caused by reactions between the amino acid side chains on the enzyme and substrate impurity constituents which cause enzyme degradation. However, different enzymes have different amino acid side chains involved in enzyme denaturation. Hence, the present approach contemplates screening amino acids, peptides, polypeptides or proteins for their ability to react with isolated substrate impurity constituents and hence serve as an initial substrate purification media to increase enzymatic half-life. Such screening can also be done with initial substrate which contains the substrate impurity constituents. Alternatively, the present approach contemplates using amino acids or peptides or polypeptides for initial substrate purification where it is known that one or more particular amino acid residues are prone to reacting with substrate impurities where the reactions result in inactivating enzyme. Thus, amino acids, peptides or polypeptides can have a protective effect for enzymes by functioning as a "trap" to react and remove inactivating compounds in the substrates, preventing the enzymes from being denatured by the compounds. Trapping of the inactivating compounds may also provide a means to concentrate the inactivating compounds for recovery and use, such as use as selective enzyme inactivators.

Amino acids consist of an amino group and a carboxyl group, both bonded to a carbon atom, which is called the alpha-carbon. The alpha-carbon is typically further bonded to a hydrogen and an R group, referred to as a side chain. However, the alpha carbon can also be bonded to two R groups. Side chains vary in size, shape, charge, hydrogen-bonding capacity and chemical reactivity. Side chains can be apolar, polar, charged or uncharged. Some amino acids have basic side chains with more than one amino group. Examples of such amino acids include lysine, arginine and histidine. Asparagine and glutamine have amide side chains. Cysteine and methionine have sulfur-containing side chain. The amino group (bonded to the alpha-carbon, or part of the R group side chain) can be a primary, secondary or tertiary amino group. Any amino acid can be used according to the present approach, including artificial and isomeric amino acids.

Except for usage in the context of a residue which is part of a peptide, polypeptide or protein, "amino acid" as used herein refers to an amino acid not bound to other amino acids via a peptide linkage (or, via an amide bond). Except for usage in the context of residues which are part of a peptide, polypeptide or protein, "one or more amino acids" as used herein refers to one or more types of amino acids, wherein the amino acids are not bound to each other via a peptide linkage (or, via an amide bond). Peptides, polypeptides and proteins all contain more than one amino acid covalently bound to each other through amide bonds (—NH—C(O)CHR—, where R is the R group bound to the alpha carbon). Peptides and polypeptides can be comprised of the same or different types of amino acid residues (i.e., amino acids having the same or different types of R groups attached to the alpha carbon).

Non-limiting examples of amino acids useful according to the present include alanine, valine, leucine, isoleucine, proline, phenylalanine, tryptophan, methionine, glycine, serine, threonine, cysteine, tyrosine, asparagine, glutamine, aspartic acid, glutamic acid, lysine, arginine, histidine, 2-aminoadiic acid, 3-aminoadipic acid, beta-alanine, 2-aminobutyric acid, 4-aminobutyric acid, 6-aminocaproic acid, 2-aminoheptanoic acid, 2-aminoisobutyric acid, 3-aminoisobutyric acid, 2-aminopimelic acid, 2,4 diaminobutyric acid, desmosine, 2,2'-diaminopimelic acid, 2,3-diaminopropionic acid, N-ethylglycine, N-ethylasparagine, hydroxylysine, allohydroxylsine, 3-hydroxyproline, 4-hydroxyproline, isodesmosine, allo-isoleucine, N-methylglycine, N-methylisoleucine, 6-N-methyllysine, N-methylvaline, norvaline, norleucine, and ornithine. Amino acids can be of the conventional levulorotary stereoisomer, or of the dextrorotary stereoisomer. In a preferred embodiment, the amino acid is arginine, lysine, histidine or cysteine.

As used herein, the term "protein material" is used herein to refer to and encompass peptides, polypeptides and proteins. For example, the term "one or more protein materials" is intended to refer to one or more peptides, polypeptides, and/or proteins.

Another aspect of the present approach is amino acids, peptides, polypeptides or proteins coated on support carriers to increase the contact surface area. Amino acids are not oil soluble and cannot be dispersed well in the oil substrate for reaction with the inactivating impurities in the substrate oil. Amino acids are not porous material either. Large surface area is beneficial for an efficient contact between the amino acids and impurities. Another advantage of using support carriers is the cost. Support carriers are usually cheaper than amino acids. As used herein, "coated" refers to a coating that results from mixing, adsorbing, absorbing, covalently bonding, hydrogen bonding or ionically associating amino acids, peptides, polypeptides or proteins to the support carriers.

Non-limiting examples of solid support carriers include activated carbon, coal activated carbon, wood activated carbon, peat activated carbon, coconut shell activated carbon, natural minerals, processed minerals, montmorillonite, attapulgite, bentonite, palygorskite, Fuller's earth, diatomite, smectite, hormite, quartz sand, limestone, kaolin, ball clay, talc, pyrophyllite, perlite, silica, sodium silicate, silica hydrogel, silica gel, fumed silica, precipitated silica, colloidal silica, dialytic silica, fibrous materials, cellulose, cellulose esters, cellulose ethers, microcrystalline cellulose; alumina, zeolite, starches, molecular sieves, previously used immobilized lipase, diatomaceous earth, ion exchange resin, size exclusion chromatography resin, chelating resins, chiral resins, rice hull ash, reverse phase silica, and bleaching clays. The purification medium can be resinous, granulated, particulate, membranous or fibrous.

Preferably, the solid support is relatively inexpensive and has a large surface area. Non-limiting examples of such supports include activated carbons, natural minerals (such as clays), processed minerals (such as acid activated clays), diatomite, kaolin, talc, perlite, various silica products, alumina, zeolite, starches, molecular sieves, quartz sand, limestone, fibrous materials (such as cellulose, or microcrystalline cellulose), diatomaceous earth, rice hull ash and ion exchange resins.

The present approach also relates to using protein as a substrate purification medium. The protein can be vegetable protein (for example, soy protein), textured vegetable protein (for example, textured soy protein) and/or other proteins, such as whey protein. In particular, the present approach is directed to using such a protein to purify the initial substrate prior to contacting the substrate with lipase. In one embodiment of the present approach, textured vegetable protein is used. Textured vegetable protein has a rigid texture and an expanded, open structure which provides greater surface area to interact with oil, thus conferring substantial advantages over conventional protein in its use for oil treatment.

In contrast, amino-groups in conventional peptides or proteins (such as those described in JP 08-140689 A2) are bound and not as readily available to react with secondary oxidation products. In a non-aqueous matrix, ionic forces holding proteins together tend to be at least an order of magnitude greater than other forces (e.g., van der Waals interactions or hydrogen bonding). Conventional proteins in a non-aqueous matrix tend to clump together and present the smallest possible total surface area to the non-aqueous medium. Thus, conventional proteins minimize the amino groups available for interaction with the oil components believed to cause enzyme inactivation. Hence, amino acids of conventional proteins are relatively impenetrable (and unavailable) to oils and other non-aqueous media, and do not as readily react with the oil components believed to cause enzyme inactivation.

The proteins used according to the present approach provide advantages over conventional proteins. According to one embodiment of the present approach, TVP® brand textured vegetable protein available from Archer-Daniels-Midland Company of Decatur, Ill. is used. The moisture content of this product is typically about 6%. Advantages conferred by the texturizing process include particle rigidity and increased surface area relative to the untextured protein. Other treatments such as typical soybean expanders and collet forming devices may also be used to confer desired properties on protein.

Good contact between the initial substrate and a protein substrate purification medium can be facilitated by using a protein which is relatively dry. Thus, in one embodiment, the moisture content of the protein (for example a vegetable protein or a textured vegetable protein) is less than about 5%. For example, the moisture content of the protein can be from about 0% to about 5%, or any amount between about 0% and about 5% (e.g. about 0%, about 1%, about 2%, about 3%, about 4%, or about 5%), or any range between about 0% and about 5% (e.g. about 2% to about 4%).

The moisture range of the protein (for example a vegetable protein or a textured vegetable protein) can be controlled during manufacture to give the desired moisture content. Alternatively, the moisture content of the protein can be adjusted after manufacture, for example by oven drying or contact with a solvent that removes some of the moisture from the textured vegetable protein. Moisture can be removed by other known methods, such as by washing with anhydrous solvents. For example, the moisture content of textured vegetable protein containing 6% moisture can be reduced by washing with anhydrous ethanol. Ethanol-washed textured vegetable protein can be rinsed with a solvent that has good miscibility with triacylglycerols, such as acetone, ethyl acetate, or hexane.

The typical composition of the soybean is about 18% oil, about 38% protein, about 15% insoluble carbohydrate (dietary fiber), about 15% soluble carbohydrate (sucrose, stachyose, raffinose, others) and about 14% moisture, ash and other. See, e.g., Egbert, W. R., "Isolated soy protein: Technology, properties, and applications," in Soybeans as Functional Foods and Ingredients, 134-163 (KeShun L., ed., AOCS Press, Champaign, Ill. 2004). Textured soy protein is made by first cracking soybeans to remove the hull and rolling the beans into full-fat flakes. The rolling process disrupts the oil cell, facilitating solvent extraction of the oil. After the oil has been extracted, the solvent is removed and the flakes are dried, creating defatted soy flakes. The defatted flakes can then be ground to produce soy flour, sized to produce soy grits or texturized to produce textured soy protein such as Archer-Daniels-Midland Company's TVP® brand textured vegetable protein. The defatted flakes can be further processed to produce soy protein concentrates and isolated soy protein. This is accomplished by the removal of the carbohydrate components of the soybean followed by drying.

Soy proteins are generally classified into three groups: soy flours, soy protein concentrates and isolated soy proteins with minimum protein contents of about 50%, about 65% and about 90% (dry basis), respectively. Soy flours are sold as either fine powders or grits with a particle size ranging from 0.2 to 5 mm. These products can be manufactured using minimal heat to maintain the inherent enzyme activity of the soybean, or lightly to highly toasted to reduce or eliminate the active enzymes. Soy flours and grits have been traditionally used as an ingredient in the bakery industry.

Soy protein concentrates are traditionally manufactured using aqueous-alcohol to remove the soluble sugars from the defatted soy flakes (soy flour). This process results in a protein with low solubility and a product that can absorb water but lacks the ability to gel or emulsify fat.

Traditional alcohol washed concentrates are used for protein fortification of foods as well as in the manufacture of textured soy protein concentrates. Functional soy protein concentrates bind water, emulsify fat and form a gel upon heating. Functional soy protein concentrates can be produced from alcohol-washed concentrate using heat and homogenization followed by spray-drying; or produced using a water-wash process at an acidic pH to remove the soluble sugars followed by neutralization, thermal processing, homogenization and spray-drying. Functional soy protein concentrates are widely used in the meat industry to bind water and emulsify fat. These proteins are also effective in stabilizing high fat soups and sauces.

Textured or structured soy proteins can be made from soy flour, soy protein concentrate or isolated soy protein. TVP® brand textured vegetable protein is manufactured through thermoplastic extrusion of soy flour under moist heat and high pressure. The skilled artisan is familiar with the varieties of textured vegetable protein. Textured soy protein concentrate is produced from soy protein concentrate powders using similar manufacturing technology to Archer-Daniels-Midland Company's TVP® brand textured vegetable protein. Unique textured protein products can be produced using combinations of soy protein or other powdered protein ingredients such as wheat gluten in combination with various carbohydrate sources (e.g. starches). The skilled artisan is familiar with the textured products manufactured by thermoplastic extrusion technology. Such products are distributed throughout the world in the dry form. These products are hydrated in water or flavored solutions prior to usage in processed meat products, vegetarian analogs or used alone in other finished food products to simulate meat. Spun fiber technology can be used to produce a fibrous textured protein from isolated soy protein with a structure closely resembling meat fibers.

Isolated soy proteins can be manufactured from defatted soy flakes by separation of the soy protein from both the soluble and insoluble carbohydrate of the soybean.

Soy protein suitable for use in the present approach includes Archer-Daniels-Midland Company's TVP® brand textured vegetable protein (Decatur, Ill.). Such soy protein is a product of commerce containing nominally about 53% protein, about 3% fat, about 18% total dietary fiber, about 30% carbohydrates and about 9% maximum moisture. This material is available in a variety of textures, sizes and colors and is used in the food industry as a substitute for ground meat in beef patties, sausage, vegetarian foods, meatloaf mix and other similar food applications. A preferred product is Archer-Daniels-Midland Co. product code 165 840, which is supplied as pale yellow granules of about 1/16 inch diameter.

Soy protein manufactured according to other processes is also useful in the present approach. For example, the soy protein can also be the textured vegetable proteins described in U.S. Pat. Nos. 4,103,034 and 4,153,738, which are hereby incorporated by reference.

The present approach also relates to using an unmodified purification medium to reduce within a fat or oil substrate the constituents which cause or arise from fat or oil degradation. Accordingly, the method of making an esterified, transesterified or interesterified product can further comprise contacting the initial substrate (fats or oils alone, or mixed with additional components such as esters, free fatty acids or alcohols) with one or more types of unmodified purification media thereby producing a purification media-processed substrate. The purification media can contact the substrate in one or more columns or in one or more batch slurry type reactions. The purification medium preferably comes into contact with the substrate before the substrate comes into contact with the enzyme. Any of the purification media and methods of use described in U.S. Patent Application Publication No. 2003/0054509 A1 can be used along with the present approach, and are hereby incorporated by reference.

Deodorization can be used along with the purification techniques described by the present approach. Examples of deodorization processes include the deodorization techniques described by O. L. Brekke, *Deodorization, in Handbook of Soy Oil Processing and Utilization*, Erickson, D. R. et al. eds., pp. 155-191 published by the American Soybean Association and the American Oil Chemists' Society; or by Bailey's Industrial Oil and Fat Products, 5th ed., Vol. 2 (pp. 537-540) and Vol. 4 (pp. 339-390), Hui, Y. H. ed., published by John Wiley and Sons, Inc. Deodorization at ambient temperature can also be used as it will remove air from oil, which causes oxidation of oil. Other deodorization processes are described in U.S. Pat. Nos. 6,172,248 and 6,511,690; and in U.S. Patent Application Publication No. 2005/0014237 A1. All of these deodorization techniques are hereby incorporated by reference. In a preferred embodiment, the pretreatment methods of the present approach obviate the need for deodorization of substrate before contacting with the lipase.

The present approach also contemplates preventing oxidation of the substrate oil by keeping the oil under inert gases, such as nitrogen, carbon dioxide or helium during or after purification. The esterified, transesterified or interesterified products of the present approach can also be deodorized after the treatment with enzyme.

For purposes herein, the term "initial substrate" includes refined or unrefined, bleached or unbleached and/or deodorized or non-deodorized fats or oils. The fats or oils can comprise a single fat or oil or combinations of various fats or oils. According to the present approach, a substrate can be recycled (i.e., deodorized, contacted with purification media, esterified, transesterified or interesterified more than once). Hence, the skilled artisan would recognize that "initial substrate" includes i) substrates that have never been deodorized, ii) substrates that have been deodorized one or more times, iii) substrates that have never contacted purification media, iv) substrates that have contacted purification media one or more times, v) substrates that have never been esterified, transesterified or interesterified, and vi) substrates that have been esterified, transesterified or interesterified one or more times. The esterification, transesterification or interesterification process may be catalyzed enzymatically, such as with a lipase, or chemically, such as with alkali or alkoxide catalysts.

The terms "purification media-processed substrate" or "purified substrate" refer to a substrate which has contacted one or more purification media at least once. Prior to its contact with enzyme, an initial substrate or a purification media-processed substrate can be mixed with additional components including esters, free fatty acids or alcohols. These esters, free fatty acids or alcohols which are added to the initial substrate or purification media-processed substrate can optionally contact purification media prior to contacting enzyme.

The terms "product" and "esterified, transesterified or interesterified product" are used interchangeably and include esterified, transesterified or interesterified fats, oils, triglycerides, diglycerides, monoglycerides, mono- or polyhydroxyl alcohols, or esters of mono- or polyhydroxyl alcohols produced via the enzymatic transesterification or esterification process. The term "product" as used herein, has come into contact at least once with an enzyme capable of causing esterification, transesterification or interesterification. A product can be a fluid or solid at room temperature, and is increased in its proportional content of esterified, transesterified or interesterified fats, oils, triglycerides, diglycerides, monoglycerides, mono- or polyhydroxyl alcohols, or esters of mono- or polyhydroxyl alcohols as a result of its having contacted the transesterification or esterification enzyme. Esterified, transesterified or interesterified product is to be distinguished from the contents of initial substrate or purification-media processed substrate, in that product has undergone additional enzymatic transesterification or esterification reaction. The present approach contemplates use of any combination of the deodorization, purification and transesterification or esterification processes for the production of esterified, transesterified or interesterified fats, oils, triglycerides, diglycerides, monoglycerides, mono- or polyhydroxyl alcohols, or esters of mono- or polyhydroxyl alcohols.

The term "enzyme" as used in the method of the present approach includes but is not limited to lipases, as discussed herein, or any other enzyme capable of causing modifying fats or oils, such as by esterification, transesterification or interesterification of substrate. Other enzymes capable of modifying fats and oils include but are not limited to oxidoreductases, peroxidases, and esterases.

Fats and oils are composed principally of triglycerides made up of a glycerol backbone in which the hydroxyl groups are esterified with carboxylic acids. Whereas solid fats tend to be formed by triglycerides having saturated fatty acids, triglycerides with unsaturated fatty acids tend to be liquid (oils) at room temperature. Monoglycerides and diglycerides, having respectively one fatty acid ester and two alcoholic groups or two fatty acid esters and one alcoholic group, are also found in fats and oils to a lesser extent than triglycerides.

Glycerides useful in the present approach include molecules of the chemical formula $CH_2RCHR'CH_2R''$ wherein R, R' and R'' are alcohols (OH) or fatty acid groups given by —OC(═O)R''', wherein R''' is a saturated, unsaturated or polyunsaturated, straight or branched carbon chain with or without substituents. R, R', R'' and the fatty acid groups on a given glyceride can be the same or different. The acid groups R, R' and R'' can be obtained from any of the free fatty acids described herein. Glycerides for the present approach include triglycerides in which R, R' and R'' are all fatty acid groups, diglycerides in which two of R, R' and R'' are fatty acid groups and one alcohol functionality is present; monoglycerides in which one of R, R' and R'' is a fatty acid group and two alcohol functionalities are present; and glycerol in which each of R, R' and R'' is an alcohol group. Glycerides useful as starting materials of the present approach include natural fats and oils, processed fats and oils, refined fats and oils, refined and bleached fats and oils, refined, bleached and deodorized fats and oils, expelled fats and oils, and synthetic fats and oils. The process can also be carried out on in the presence of a substrate in contact with a solvent. An example is soybean oil miscella, which is the product of solvent extraction of soybean oil and often comprises crude soybean oil in hexane. Examples of refined fats and oils are described herein and in Stauffer, C., *Fats and Oils*, Eagan Press, St. Paul, Minn. (1996). Examples of processed fats and oils are refined, refined and bleached, hydrogenated and fractionated fats and oils.

The terms "fatty acid groups" or "acid groups" both refer to chemical groups given by —OC(═O)R'''. Such "fatty acid groups" or "acid groups" are connected to the remainder of the glyceride via a covalent bond to the oxygen atom that is singly bound to the carbonyl carbon. In contrast, the terms "fatty acid" or "free fatty acid" both refer to HOC(═O)R''' and are not covalently bound to a glyceride. In "fatty acid groups," "acid groups," "free fatty acids," and "fatty acids," R''' is a saturated, unsaturated or polyunsaturated, straight or branched carbon chain with or without substituents, as discussed herein. The skilled artisan will recognize that R''' of the "free fatty acids" or "fatty acids" (i.e., HOC(═O)R''') described herein are useful as R''' in the "fatty acid groups" or "acid groups" attached to the glycerides or to other esters used as substrates in the present approach. That is, a substrate of the present approach can comprise fats, oils or other esters having fatty acid groups formed from the free fatty acids or fatty acids discussed herein.

The one or more unrefined and/or unbleached fats or oils can comprise butterfat, cocoa butter, cocoa butter substitutes, illipe fat, kokum butter, milk fat, mowrah fat, phulwara butter, sal fat, shea fat, borneo tallow, lard, lanolin, beef tallow, mutton tallow, tallow or other animal fat, canola oil, castor oil, coconut oil, coriander oil, corn oil, cottonseed oil, hazelnut oil, hempseed oil, Jatropha oil, linseed oil, mango kernel oil, meadowfoam oil, mustard oil, neat's foot oil, olive oil, palm oil, palm kernel oil, palm olein, palm stearin, palm kernel olein, palm kernel stearin, peanut oil, rapeseed oil, rice bran oil, safflower oil, sasanqua oil, soybean oil, sunflower seed oil, tall oil, tsubaki oil, vegetable oils, marine oils which can be converted into plastic or solid fats such as menhaden oil, candlefish oil, cod-liver oil, orange roughy oil, pile herd oil, sardine oil, whale and herring oils, 1,3-dipalmitoyl-2-monooleine (POP), 1 (3)-palmitoyl-3(1)-stearoyl-2-monooleine (POSt), 1,3-distearoyl-2-monooleine (StOSt), triglyceride, diglyceride, monoglyceride, behenic acid triglyceride, trioleine, tripalmitine, tristearine, triglycerides of medium chain fatty acids, or combinations thereof.

Processed fats and oils such as hydrogenated or fractionated fats and oils can also be used. Examples of fractionated fats include palm olein, palm stearin, palm kernel olein, and palm kernel stearin. Fully or partially hydrogenated, saturated, unsaturated or polyunsaturated forms of the above listed fats, oils, triglycerides or diglycerides are also useful for the present approach. For the method of this approach, the described fats, oils, triglycerides or diglycerides are usable singly, or at least two of them can be used in admixture.

"Esterification" or "transesterification" are the processes by which a fatty acid group is added, repositioned or replaced on one or more components of the substrate. The acid group can be derived from a fat or oil which is part of the initial substrate, or from a free fatty acid or ester that has been added to the initial substrate or purification media-processed substrate.

The term "esterification" includes the process in which R, R' or R" on a glyceride is converted from an alcoholic group (OH) to a fatty acid group given by —OC(═O)R'". The fatty acid group which replaces the alcoholic group can come from the same or different glyceride, or from a free fatty acid or ester that has been added to the initial substrate or the purification media-processed substrate. The present approach also contemplates esterification of alcohols which have been added to the initial substrate or the purification media-processed substrate. For example, an alcohol so added may be esterified by an added free fatty acid or by a fatty acid group present on a glyceride which was a component of the initial substrate. A non-limiting example of esterification includes reaction of a free fatty acid with an alcohol.

Esterification also includes processes pertaining to the manufacture of biodiesel, such as discussed in U.S. Pat. Nos. 5,578,090; 5,713,965; and 6,398,707, which are hereby incorporated by reference. The term "biodiesel" includes lower alkyl esters of fatty acid groups found on animal or vegetable glycerides. Lower alkyl esters include methyl ester, ethyl ester, n-propyl ester, and isopropyl ester. In the production of biodiesel, the initial substrate comprises fats or oils. One or more lower alcohols (e.g., methanol, ethanol, n-propanol and isopropanol) are added to this substrate and the mixture then comes into contact with enzyme. The enzyme causes the alcohols to be esterified with the fatty acid groups which is part of the fat or oil glycerides. For example, R, R' or R" on a glyceride is a fatty acid group given by —OC(═O)R'". Upon esterification of methanol, the biodiesel product is $CH_3C(=O)R'''$. Biodiesel products also include esterification of lower alcohols with free fatty acids or other esters which are added to the initial substrate or purification media-processed substrate.

The term "transesterification" includes the process in which R, R' or R" on a glyceride is a first fatty acid group given by —OC(═O)R'", and the first fatty acid group is replaced by a second, different fatty acid group. The second fatty acid group which replaces the first fatty acid group can come from the same or different fat or oil present in the initial substrate. The second fatty acid can also come from a free fatty acid or ester added to the initial substrate or the purification media-processed substrate. The present approach also contemplates transesterification or interesterification of esterified alcohols or other esters which have been added to the initial substrate or the purification media-processed substrate. For example, an alcohol so added may be transesterified or interesterified by an added free fatty acid, by a fatty acid group on an added ester, or by a fatty acid group present on a glyceride which was a component of the initial substrate. A non-limiting example of transesterification includes reaction of a fat or oil with an alcohol (e.g., methanol) or with an ester.

The term "interesterification" includes, for example, the processes acidolysis, alcoholysis, glycerolysis, and transesterification. Examples of these processes are described herein, and in Fousseau, D. and Marangoni, A. G., "Chemical Interesterification of Food Lipids: Theory and Practice," in *Food Lipids Chemistry, Nutrition, and Biotechnology, Second Edition, Revised and Expanded*, Akoh, C. C. and Min, D. B. eds., Marcel Dekker, Inc., New York, N.Y., Chapter 10, which is hereby incorporated by reference. Acidolysis includes the reaction of a fatty acid with an ester, such as a triacylglycerol; alcoholoysis includes the reaction of an alcohol with an ester, such as a triacylglycerol; and glycerolyis includes alcoholysis reactions in which the alcohol is glycerol. A non-limiting example of interesterification or transesterification includes reactions of different triglycerides resulting in rearrangement of the fatty acid groups in the resulting glycerides and triglycerides.

An esterified, transesterified or interesterified product has respectively undergone the esterification, transesterification or interesterification process. The present approach relates to enzymes capable of effecting the esterification, transesterification or interesterification process for fats, oils, triglycerides, diglycerides, monoglycerides, free fatty acids, mono- or polyhydroxyl alcohols, or esters of mono- or polyhydroxyl alcohols.

As used herein, the "half-life" of an enzyme is the time in which the enzymatic activity of an enzyme sample is decreased by half. If, for example, an enzyme sample decreases its relative activity from 100 units to 50 units in 10 minutes, then the half life of the enzyme sample is 10 minutes. If the half-life of this sample is constant, then the relative activity will be reduced from 100 to 25 in 20 minutes (two half lives), the relative activity will be reduced from 100 to 12.5 in 30 minutes (three half lives), the relative activity will be reduced from 100 to 6.25 in 40 minutes (four half lives), etc. As used herein, the expression "half-life of an enzyme" means the half-life of an enzymatic sample.

A "prolonged" half-life refers to an increased "half-life". Prolonging the half-life of an enzyme results in increasing the half life of an enzyme by about 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 95%, 100%, 105%, 110%, 115%, 120%, 125%, 130%, 135%, 140%, 145%, 150%, 155%, 160%, 165%, 170%, 175%, 180%, 185%, 190%, 195%, 200%, 210%, 220%, 230%, 240%, 250%, 260%, 270%, 280%, 290%, 300%, 320%, 340%, 360%, 380%, 400%, 420%, 440%, 460%, 480%, 500% or more as compared to the half-life of an enzyme used in an esterified, transesterified or interesterified fat or oil producing process which does not employ a purification medium.

Non-limiting examples of "constituents which cause or arise from fat or oil degradation" include oxidative or oxidating species, reactive oxygen species, fat or oil oxidation products, peroxides, ozone ($O_3$), $O_2$, superoxide, free fatty acids, volatile organic compounds, free radicals, trace metals, and natural prooxidants such as chlorophyll. Such constituents also include other characterized or uncharacterized compounds recognized by the skilled artisan to cause or arise from fat or oil degradation. Such constituents can arise from oxidation pathways, or from other pathways recognized by the skilled artisan to result in fat or oil degradation. "Reducing" the constituents which cause or arise from fat or oil degradation in a substrate sample refers to lowering the concentration, percentage or types of such constituents in the sample.

The method of making an esterified, transesterified or interesterified product can further comprise mixing the initial substrate and/or the purification media-processed substrate with the enzyme in one or more tanks for a batch slurry reaction, or flowing the initial substrate and/or the purification media-processed substrate through a column containing the enzyme. A bed of the one or more types of purification media can be placed upon a bed of the enzyme within a column upstream from the enzyme.

The initial substrate, the purification media-processed substrate, the esterified, transesterified or interesterified product and the enzyme can be in an inert gas environment. The inert gas can be selected from the group consisting of $N_2$, $CO_2$, He, Ar, and Ne. Preferably, the methods of the present approach further comprise preventing oxidative degradation of the initial substrate, the purification media-processed substrate, the esterified, transesterified or interesterified product or the enzyme. The method of making an esterified, transesterified or interesterified product can further comprise preventing oxidative degradation to the initial substrate, the purification media-processed substrate, the esterified, transesterified or interesterified product or the enzyme.

The skilled artisan would recognize that in respect to the method of making an esterified, transesterified or interesterified product, any combination of the above described particulars pertaining to deodorization options (e.g., flow rate, residence or holding time, temperature, pressure, choice of inert gas), initial substrate, components (e.g., free fatty acids, nonglyceride esters, alcohols) optionally added to the initial substrate or the purification media-processed substrate, enzyme, monitoring or adjusting methods, fats or oils produced, use of columns or batch slurry reactions, and purification medium are useful in the present approach.

Transesterification, esterification or interesterification according to the present approach is effected by a lipase. The lipase can be specific or unspecific with respect to its substrate. The initial substrate can be composed of one or more types of fat or oil and have its physical properties modified in an esterification, transesterification or interesterification process. Nonselective enzymes cause rearrangement by transesterification at all three positions on a glyceride and may result in randomization at thermodynamic equilibrium; but 1,3-specific lipases cause rearrangements preferably at the sn-1 and sn-3 positions on a glyceride. For example, when a blend of olive oil and fully hydrogenated palm kernel oil is treated with a non-selective enzyme, the components of the product have different physical properties from either of the initial substrates. Both 1,3-specific lipases and nonselective lipases are capable of this rearrangement process.

Preferably, the lipase is a 1,3-selective lipase, which preferably catalyzes esterification or transesterification of the terminal esters in the sn-1 and sn-3 positions of a glyceride. The lipase can also be a non-selective, nonspecific lipase. The process can produce esterified, transesterified or interesterified fats with no or reduced trans fatty acids for margarine, shortening, and other confectionery fats such as cocoa butter substitute. The esterified, transesterified or interesterified product can also be a 1,3-diglyceride, such as those disclosed in U.S. Pat. No. 6,004,611.

The enzyme used according to the present approach can be a lipase obtained from a cultured eukaryotic or prokaryotic cell line or animal tissue. Such lipases typically fall into one of three categories (Macrae, A. R., *J.A.O.C.S.* 60:243A-246A (1983)). The first category includes nonspecific lipases capable of releasing or binding any fatty acid group from or to any glyceride position. Such lipases have been obtained from *Candida cylindracae, Corynebacterium acnes* and *Staphylococcus aureus* (Macrae, 1983; U.S. Pat. No. 5,128,251). The second category of lipases only adds or removes specific fatty acid groups to or from specific glycerides. Thus, these lipases are useful in producing or modifying specific glycerides. Such lipases have been obtained from *Geotrichum candidium* and *Rhizopus, Aspergillus*, and *Mucor* genera (Macrae, 1983; U.S. Pat. No. 5,128,251). The last category of lipases preferably catalyze the removal or addition of fatty acid groups from the glyceride carbons on the end in the 1- and 3-positions. Such lipases have been obtained from *Thermomyces lanuginosa, Rhizomucor miehei, Aspergillus niger, Mucor javanicus, Rhizopus delemar*, and *Rhizopus arrhizus* (Macrae, 1983). Enzymes from animal sources, such as pig pancreas lipase, can also be used.

There are many microorganisms from which lipases useful in the present approach are obtained. U.S. Pat. No. 5,219,733 lists examples of such microorganisms including those of the genus *Achromobacter* such as *A. iofurgus* and *A. lipolyticum*; the genus *Chromobacterium* such as *C. viscosum* var. *paralipolyticum*; the genus *Corynebacterium* such as *C. acnes*; the genus *Staphylococcus* such as *S. aureus*; the genus *Aspergillus* such as *A. niger* and *A. oryzae*; the genus *Candida* such as *C. cylindracea, C. antarctica* b, *C. rosa* and *C. rugosa*; the genus *Humicora* such as *H. lanuginosa*; the genus *Penicillium* such as *P. caseicolum, P. crustosum, P. cyclopium* and *P. roqueforti*; the genus *Torulopsis* such as *T. ernobii*; the genus *Mucor* such as *M. miehei, M. japonicus* and *M. javanicus*; the genus *Bacillus* such as *B. subtilis*; the genus *Thermomyces* such as *T. ibadanensis* and *T. lanuginosa* (see Zhang, H. et al. *J.A.O.C.S.* 78: 57-64 (2001)); the genus *Rhizopus* such as *R. delemar, R. japonicus, R. arrhizus* and *R. neveus*; the genus *Pseudomonas* such as *P. aeruginosa, P. fragi, P. cepacia, P. mephitica* var. *lipolytica* and *P. fluorescens*; the genus *Alcaligenes*; the genus *Rhizomucor* such as *R. miehei*; the genus *Humicolo* such as *H. rosa*; and the genus *Geotrichum* such as *G. candidum*. Several lipases obtained from these organisms are commercially available as purified enzymes. The skilled artisan would recognize other enzymes capable of affecting esterification, transesterification or interesterification including other lipases useful for the present approach.

Lipases obtained from the organisms above are immobilized for the present approach on suitable carriers by a usual method known to persons of ordinary skill in the art. U.S. Pat. Nos. 4,798,793; 5,166,064; 5,219,733; 5,292,649; and 5,773,266 describe examples of immobilized lipase and methods of preparation. Examples of methods of preparation include the entrapping method, inorganic carrier covalent bond method, organic carrier covalent bond method, and the adsorption method. The lipase used in the examples below were obtained from Novozymes (Denmark) but can be substituted with purified and/or immobilized lipase prepared by others. The present approach also contemplates using crude enzyme preparations or cells of microorganisms capable of over expressing lipase, a culture of such cells, a substrate enzyme solution obtained by treating the culture, or a composition containing the enzyme. The present approach also contemplates the use of more than one enzyme preparation, such as more than one lipase preparation.

U.S. Pat. Nos. 4,940,845 and 5,219,733 describe the characteristics of several useful carriers. Useful carriers are preferably microporous and have a hydrophobic porous surface. Usually, the pores have an average radius of about 10 Å to about 1,000 Å, and a porosity from about 20 to about 80% by volume, more preferably, from about 40 to about 60% by volume. The pores give the carrier an increased enzyme bonding area per particle of the carrier. Examples of preferred inorganic carriers include porous glass, porous ceramics, celite, porous metallic particles such as titanium oxide, stainless steel or alumina, porous silica gel, molecular sieve, active carbon, clay, kaolinite, perlite, glass fibers, diatomaceous earth, bentonite, hydroxyapatite, calcium phosphate gel, and alkylamine derivatives of inorganic carriers. Examples of preferred organic carriers include microporous Teflon, aliphatic olefinic polymer (e.g., polyethylene, polypropylene, a homo- or copolymer of styrene or a blend thereof or a pretreated inorganic support) nylon, polyamides, polycarbonates, nitrocellulose and acetylcellulose. Other suitable organic carriers include hydrophillic polysaccharides such as agarose gel with an alkyl, phenyl, trityl or other similar hydrophobic group to provide a hydrophobic porous surface (e.g., "Octyl-Sepharose CL-4B", "Phenyl-Sepharose CL-4B", both products of Pharmacia Fine Chemicals (Kalamazoo, Mich.). Microporous adsorbing resins include those made of styrene or alkylamine polymer, chelate resin, ion exchange resin such a "DOWEX MWA-1" (weakly basic anion exchange resin manufactured by the Dow Chemical Co., having a tertiary amine as the exchange group, composed basically of polystyrene chains cross linked with divinylbenzene, 150 Å in average pore radius and 20-50 mesh in particle size), and hydrophilic cellulose resin such as one prepared by masking the hydrophilic group of a cellulosic carrier, e.g., "Cellulofine GC700-m" (product of Chisso Corporation (Tokyo, Japan), 45-105 μm in particle size).

The esterification, transesterification or interesterification can be conducted in a column or in batch slurry type reactions as described in the Examples section below. In the batch slurry reactions, the enzyme and substrates are mixed vigorously to ensure a good contact between them, taking care not to mix under high shear, which could cause loss of enzyme activity. Preferably, the transesterification or esterification reaction is carried out in a fixed bed reactor with immobilized lipases.

The fatty acid groups described herein can be added to the initial substrate or the purification media-processed substrate to esterify alcoholic groups present on glycerides of the initial substrate, or alcoholic groups of other compounds (e.g., alcohols or esters) added to the purification media-processed substrate. Glycerides having any of the fatty acid groups as described herein can also be used in the initial substrate; and other esters having any of the fatty acid groups described herein can be added to the initial substrate or purification media-processed substrate. Such fatty acids include saturated straight-chain or branched fatty acid groups, unsaturated straight-chain or branched fatty acid groups, hydroxy fatty acid groups, and polycarboxylic acid groups, or contain non-carbon substituents including oxygen, sulfur or nitrogen. The fatty acid groups can be naturally occurring, processed or refined from natural products or synthetically produced. Although there is no upper or lower limit for the length of the longest carbon chain in useful fatty acids, it is preferable that their length is about 6 to about 34 carbons long. Specific fatty acid groups useful for the present approach can be formed from the fatty acids described in U.S. Pat. Nos. 4,883,684; 5,124,166; 5,149,642; 5,219,733; and 5,399,728.

Examples of useful saturated straight-chain fatty acid groups having an even number of carbon atoms can be formed from the fatty acids described in U.S. Pat. No. 5,219,733 including acetic acid, butyric acid, caproic acid, caprylic acid, capric acid, lauric acid, myristic acid, palmitic acid, stearic acid, arachic acid, behenic acid, lignoceric acid, hexacosanoic acid, octacosanoic acid, triacontanoic acid and n-dotriacontanoic acid, and those having an odd number of carbon atoms, such as propionic acid, n-valeric acid, enanthic acid, pelargonic acid, hendecanoic acid, tridecanoic acid, pentadecanoic acid, heptadecanoic acid, nonadecanoic acid, heneicosanoic acid, tricosanoic acid, pentacosanoic acid and heptacosanoic acid.

Examples of useful saturated branched fatty acid groups can be formed from fatty acids described in U.S. Pat. No. 5,219,733 including isobutyric acid, isocaproic acid, isocaprylic acid, isocapric acid, isolauric acid, 11-methyldodecanoic acid, isomyristic acid, 13-methyl-tetradecanoic acid, isopalmitic acid, 15-methyl-hexadecanoic acid, isostearic acid, 17-methyloctadecanoic acid, isoarachic acid, 19-methyl-eicosanoic acid, a-ethyl-hexanoic acid, a-hexyldecanoic acid, a-heptylundecanoic acid, 2-decyltetradecanoic acid, 2-undecyltetradecanoic acid, 2-decylpentadecanoic acid, 2-undecylpentadecanoic acid, and Fine oxocol 1800 acid (product of Nissan Chemical Industries, Ltd.)

Examples of useful saturated odd-carbon branched fatty acid groups can be formed from fatty acids described in U.S. Pat. No. 5,219,733 including anteiso fatty acids terminating with an isobutyl group, such as 6-methyl-octanoic acid, 8-methyl-decanoic acid, 10-methyl-dodecanoic acid, 12-methyl-tetradecanoic acid, 14-methyl-hexadecanoic acid, 16-methyl-octadecanoic acid, 18-methyl-eicosanoic acid, 20-methyl-docosanoic acid, 22-methyl-tetracosanoic acid, 24-methyl-hexacosanoic acid and 26-methyloctacosanoic acid.

Examples of useful unsaturated fatty acid groups can be formed from fatty acids described in U.S. Pat. No. 5,219,733 including 4-decenoic acid, caproleic acid, 4-dodecenoic acid, 5-dodecenoic acid, lauroleic acid, 4-tetradecenoic acid, 5-tetradecenoic acid, 9-tetradecenoic acid, palmitoleic acid, 6-octadecenoic acid, oleic acid, 9-octadecenoic acid, 11-octadecenoic acid, 9-eicosenoic acid, cis-11-eicosenoic acid, cetoleic acid, 13-docosenoic acid, 15-tetracosenoic acid, 17-hexacosenoic acid, 6,9,12,15-hexadecatetraenoic acid, linoleic acid, linolenic acid, α-eleostearic acid, α-eleostearic acid, punicic acid, 6,9,12,15-octadecatetraenoic acid, parinaric acid, 5,8,11,14-eicosatetraenoic acid, 5,8,11,14,17-eicosapentaenoic acid (EPA), 7,10,13,16,19-docosapentaenoic acid, 4,7,10,13,16,19-docosahexaenoic acid (DHA) and the like.

Examples of useful hydroxy fatty acid groups can be formed from fatty acids described in U.S. Pat. No. 5,219,733 including α-hydroxylauric acid, α-hydroxymyristic acid, α-hydroxypalmitic acid, α-hydroxystearic acid, α-hydroxylauric acid, α-hydroxyarachic acid, 9-hydroxy-12-octadecenoic acid, ricinoleic acid, α-hydroxybehenic acid, 9-hydroxy-trans-10,12-octadecadienic acid, kamolenic acid, ipurolic acid, 9,10-dihydroxystearic acid, 12-hydroxystearic acid and the like.

Examples of useful polycarboxylic acid fatty acid groups can be formed from fatty acids described in U.S. Pat. No. 5,219,733 including oxalic acid, citric acid, malonic acid, succinic acid, glutaric acid, adipic acid, pimelic acid, suberic acid, azelaic acid, sebacic acid, D,L-malic acid and the like.

Preferably, the fatty acid groups have carbon chains from about 4 to about 34 carbons long. More preferably, the fatty acid groups have carbon chains from about 4 to about 26 carbons long. Most preferably, the fatty acid groups have carbon chains from about 4 to about 22 carbons long. Preferably the fatty acid groups are formed from the following group of free fatty acids: palmitic acid, stearic acid, oleic acid, linoleic acid, linolenic acid, arachidonic acid, erucic acid, caproic acid, caprylic acid, capric acid, eicosapentanoic acid (EPA), docosahexaenoic acid (DHA), lauric acid, myristic acid, 5-eicosenoic acid, butyric acid, γ-linolenic acid and conjugated linoleic acid. Fatty acid groups formed from fatty acids derived from various plant and animal fats and oils (such as fish oil fatty acids) and processed or refined fatty acids from plant and animal fats and oils (such as fractionated fish oil fatty acids in which EPA and DHA are concentrated) can also be added. Fatty acid groups can also be formed from medium chain fatty acids (as described by Merolli, A. et al., *INFORM,* 8:597-603 (1997)). Also preferably, the fatty acid groups are formed from free fatty acids having carbon chains from about 4 to about 36, about 4 to about 24, or about 4 to about 22 carbons long.

Alcohols or esters of alcohols can also be added to the initial substrate or the purification media-processed substrate. These alcohols and esters can be esterified, transesterified or interesterified by acid groups present on glycerides of the initial substrate. Alternatively, these alcohols or esters thereof can be esterified, transesterified or interesterified by free fatty acids or esters added to the purification media-processed substrate. “Esters” include any of the alcohols described herein esterified by any of the fatty acids described herein.

Examples of useful esters other than glycerides include wax esters, alkyl esters such as methyl, ethyl, isopropyl, hexadecyl or octadecyl esters, aryl esters, propylene glycol esters, ethylene glycol esters, 1,2-propanediol esters and 1,3-propanediol esters. Esters can be formed from the esterification, transesterification or interesterification of monohydroxyl alcohols or polyhydroxyl alcohols by the free fatty acids, fats or oils as described herein.

The initial substrate or purification media-processed substrate can be mixed with monohydroxyl alcohols or polyhydroxyl alcohols prior to contact with the purification medium or the enzyme. The esterified, transesterified or interesterified product can be formed from the esterification, transesterification or interesterification of the monohydroxyl alcohols or polyhydroxyl alcohols. The monohydroxyl alcohols or the polyhydroxyl alcohols can be primary, secondary or tertiary alcohols of annular, straight or branched chain compounds. The monohydroxyl alcohols can be selected from the group consisting of methyl alcohol, isopropyl alcohol, allyl alcohol, ethanol, propanol, n-butanol, iso-butanol, sec-butanol, tert-butanol, n-pentanol, iso-pentanol, n-hexanol, hexadecyl alcohol or octadecyl alcohol. The polyhydroxyl alcohols can be selected from the group consisting of glycerol, propylene glycol, ethylene glycol, 1,2-propanediol and 1,3-propanediol.

Examples of alcohols useful in the present approach include monohydroxyl alcohols or polyhydroxyl alcohols. The monohydroxyl alcohols can be primary, secondary or tertiary alcohols of annular, straight or branched chain compounds with one or more carbons such as methyl alcohol, isopropyl alcohol, allyl alcohol, ethanol, propanol, n-butanol, iso-butanol, sec-butanol, tert-butanol, n-pentanol, iso-pentanol, n-hexanol, hexadecyl alcohol or octadecyl alcohol. The hydroxyl group can be attached to an aromatic ring, such as phenol. Examples of polyhydroxyl alcohols includes glycerol, propylene glycol, ethylene glycol, 1,2-propanediol and 1,3-propanediol.

U.S. Pat. No. 5,219,733 indicates other alcohols useful for the present approach. These alcohols include, but are not limited to 14-methylhexadecanol-1,16-methyloctadecanol-1,18-methylnonadecanol, 18-methyleicosanol, 20-methylheneicosanol, 20-methyldocosanol, 22-methyltricosanol, 22-methyltetracosanol, 24-methylpentacosanol-1 and 24-methylhexacosanol.

The one or more types of purification media and the enzyme can be packed together or separately in one or more columns through which the initial substrate, the purification-media processed substrate or the esterified, transesterified or interesterified product flows. The columns can be jacketed columns in which the temperature of one or more of the initial substrate, the purification media-processed substrate, the one or more types of purification media, the enzyme or the esterified, transesterified or interesterified product can be regulated. The purification media-processed substrate can be prepared by mixing the initial substrate with the one or more types of purification media in a tank for a batch slurry purification reaction or mixing the initial substrate in a series of tanks for a series of batch slurry purification reactions. The purification media-processed substrate can be separated from the one or more types of purification media via filtration, centrifugation or concentration prior to reacting the purification media-processed substrate with the enzyme. Preferably, the purification medium is kept separate from the enzyme. By keeping the purification medium separate from the enzyme, the impurity constituents of the initial substrate which degrade lipase do not come into contact with the lipase.

In the method of the present approach, one or more types of purification media and the lipase are packed into one or more columns. In all embodiments, the purification medium is kept separate from (i.e., not intermixed with) the active lipase. If multiple types of purification media are used, they can be mixed together and packed into a single column or kept separate in different columns. In an alternative embodiment, one or more types of purification media are placed upon a bed of packed lipase within a column. Alternatively, the active lipase can be kept separate from the purification media by packing it in its own column. More than one type of purification media can be used for purposes of removing different kinds of impurities in the initial substrate. The columns and other fluid conduits can be jacketed so as to regulate the temperature of the initial substrate, the purification media-processed substrate, the purification media or the enzyme. The purification media can be regenerated for repeated use.

Also in the method of the present approach, the purification media-processed substrate is prepared by mixing the initial substrate with one or more types of purification media in a tank for a batch slurry type purification reaction or mixing the initial substrate in a series of tanks for a series of batch slurry type purification reactions. In these batch slurry type purification reactions, the different types of purification media can be kept separate or can be combined. After reacting with one type of purification medium (or specific mixture of purification media), the initial substrate is separated from the purification medium (or media) via filtration, centrifugation or concentration. After this separation step, the initial substrate is further purified with other purification media or serves as purification media-processed substrate and is reacted with lipase. The purification media-processed substrate prepared by this batch slurry type purification reaction method can be reacted with lipase in a tank for batch slurry type transesterification or esterification. Alternatively, the purification media-processed substrate can be caused to flow through a lipase column. The reacting tanks, columns and other fluid conduits can be jacketed so as to regulate the temperature of the initial substrate, the purification media-processed substrate, the purification media or the enzyme. Other manners of temperature regulation, such as heating/cooling coils or temperature controlled rooms, are contemplated and well known in the art. The purification media can be regenerated for repeated use.

Lipase enzymatic activity is also affected by factors such as temperature, light and moisture content. Temperature is controlled as described above. Light can be kept out by using various light blocking or filtering means known in the art. Moisture content, which includes ambient atmospheric moisture, is controlled by operating the process as a closed system. Where the process includes deodorization using steam as a stripping agent, the deodorization process can be kept isolated from the enzyme. Because deodorization is performed at high temperature and under vacuum, moisture content in the deodorized oil is very low. Where the deodorization process uses an inert gas as the stripping agent, the deodorization process is optionally kept isolated from the enzyme. Alternatively, a bed of nitrogen gas (or other inert gas) can be placed on top of the bed or column containing either purification medium or enzyme. These techniques have the added benefit of keeping atmospheric oxidative species (including oxygen) away from the substrate, product or enzyme.

Immobilized lipase can be mixed with initial substrate or purification media-processed substrate to form a slurry which is packed into a suitable column. Alternatively, substrate or purified substrate can flow through a pre-packed enzyme column. The temperature of the substrate is regulated so that it can continuously flow though the column for contact with the transesterification or esterification enzyme. If solid or very viscous fats, oils, triglycerides or diglycerides are used, the substrate is heated to a fluid or less viscous state. The substrate can be caused to flow through the column(s) under the force of gravity, by using a peristaltic or piston pump, under the influence of a suction or vacuum pump, or using a centrifugal pump. The transesterified fats and oils produced are collected and the desired glycerides are separated from the mixture of reaction products by methods well known in the art. This continuous method involves a reduced likelihood of permitting exposure of the substrates to air during reaction and therefore has the advantage that the substrates will not be exposed to moisture or oxidative species. Alternatively, reaction tanks for batch slurry type production as described above can also be used. Preferably, these reaction tanks are also sealed from air so as to prevent exposure to oxygen, moisture, or other ambient oxidizing species.

The method of the present approach also comprises monitoring enzymatic activity by measuring one or more physical properties of the esterified, transesterified or interesterified product; and optionally adjusting the duration of time for which the purified substrate contacts the lipase, or adjusting the temperature of the initial substrate, the purified substrate, the one or more types of the purification medium or the lipase in response to a change in enzymatic activity, to produce fats or oils having a substantially uniform increased proportion of esterification, interesterification, or transesterification relative to the initial substrate as measured by physical properties. The duration of time for which the purified substrate contacts the lipase can be adjusted by adjusting the flow rate of purified substrate provided to contact with the lipase. Also, the amount and type of the one or more types of purification media can be adjusted in response to changes in the physical properties of the fats or oils to increase or improve enzymatic productivity of the lipase.

By the phrase "substantially uniform increased proportion of esterification, interesterification, or transesterification relative to the initial substrate," it is meant that the amount or degree of esterification, interesterification, or transesterification of the oil or fat produced from a particular initial substrate by the methods of the invention varies by no more than about 10%, preferably no more than about 5% as measured by a change in one of the physical property measurements, below.

In the present approach, changes in enzymatic activity are monitored by following changes in the physical properties of the product. As the enzymatic activity decreases, the rate of substrate conversion decreases so that less of the substrate is converted into product via esterification, transesterification or interesterification at a given flow rate than the initial amount of conversion. Consequently, as the enzymatic activity decays, the physical properties of the product increasingly resemble the physical properties of the components of the substrate. The skilled artisan recognizes that by following changes in physical properties, the parameters of the esterified, transesterified or interesterified production process can be adjusted, thereby increasing the proportion of esterified, transesterified or interesterified product relative to the substrate, so that fats and oils with a desired degree of esterification, interesterification, or transesterification can be produced while improving the enzymatic productivity of the lipase.

The one or more physical properties of the fats or oils product that can be measured during the methods of the invention include the dropping point temperature of the product, the solid fat content profile of the product, and changes in optical spectra.

The Mettler dropping point (MDP) is one example of a physical property which can be measured to follow changes in enzymatic activity. The MDP is determined using Mettler Toledo, Inc. (Columbus, Ohio) thermal analysis instruments according to the American Oil Chemists Society Official Method #Cc 18-80. The MDP is the temperature at which a mixture of fats or oils becomes fluid.

The product's solid fat content (SFC) profile (as a function of temperature) is another useful physical property for tracking changes in enzymatic activity. SFC can be measured according to American Oil Chemists Society Official Method #Cd 16b-93.

Following changes in optical spectra is another way to monitor changes in enzymatic activity. The substrate and product each have a characteristic optical spectrum. As the lipase activity decays, the amount of product that gives rise to spectroscopic signals attributable to esterified, transesterified or interesterified product (and not attributable to substrate) diminishes.

All of these properties are measured using techniques well known in the art, and are useful in following changes in enzymatic activity and for determining the uniformity of esterification, interesterification, or transesterification of the produced oils or fats.

For example, as the lipase enzymatic activity decays, less substrate is converted into product resulting in an increased substrate:product ratio. This increased ratio is manifested in a change of physical properties of the outflowing product tending towards the physical properties of the non-esterified or non-transesterified substrate. To minimize this change, the flow rate of the substrate is reduced so that it is exposed for a longer period of time to the packed lipase. The flow rate reduction increases the product:substrate ratio and consequently the physical properties of the outflowing fats or oils reflect that of the desired esterified, transesterified or interesterified product. Other process parameters that can be altered include the flow rate, temperature or pressure of the initial substrate or the purification media-processed substrate.

Where purification media-processed substrate is reacted with lipase in a tank for batch slurry type production, changes in the product's physical properties can also be monitored as described above. In a batch slurry type process, an optimized duration of time is determined for contacting the initial substrate with the purification medium (or media). An optimized time is also determined for contacting the purification media-processed substrate with enzyme.

Thus, embodiments of the invention involve monitoring enzymatic activity by measuring one or more physical properties of the product after having flowed through the lipase, adjusting flow rate, column residence time, or temperature of the initial substrate, or purification media-processed substrate, and adjusting the process parameters or the amount and type of the purification medium in response to changes in the physical properties in order to increase or improve the enzymatic productivity of the lipase and/or to increase the proportion of esterified, transesterified or interesterified fats or oils in the product so that fats and oils with a desired degree of esterification, interesterification, or transesterification can be produced, particularly those having a substantially uniform increased proportion of esterification, interesterification, or transesterification relative to the initial substrate.

The esterified, transesterified or interesterified product can be subjected to usual oil refining processes including refining, bleaching, fractionation, separation or purification process, or additional deodorization processing. The product of the present process can be separated from any free fatty acid or other by-products by refining techniques well known in the art. In the case of batch slurry type methods, the desired product can be separated using a suitable solvent such as hexane, removing the fatty acid material with an alkali, dehydrating and drying the solvent layer, and removing the solvent from the layer. The desired product can be purified, for example, by column chromatography. The desired products thus obtained are usable for a wide variety of culinary applications.

The following examples show the effect of the substrate pretreatment on the enzyme productivity.

EXAMPLES

The examples described below show that productivity of the enzymatic transesterification or esterification is improved greatly by purification of the substrate oil. The following examples are illustrative only and are not intended to limit the scope of the invention as defined by the appended claims.

Example 1

The following example shows the effect of arginine pretreatment of the substrate on lipase half-life. The following three experiments were performed in this example: i) the activity of lipase was monitored upon exposure to substrate which had undergone no arginine pre-treatment ("control"); ii) the activity of lipase was monitored upon exposure to substrate which was pretreated with granular arginine; and iii) the activity of lipase was monitored upon exposure to substrate which was pretreated with arginine-coated silica.

9.4 g of enzyme (TL IM from Novozymes A/S, Denmark) was packed in a 1.5-cm diameter jacketed column (30 cm long) at a height of 11.8 cm, which gave 20.8 ml enzyme bed volume. The water circulating through the column jacket was held at 70° C. The piston pump and feed lines were wrapped with heating tape and covered with insulation to prevent any solidification of substrate.

The pre-treatment materials (i.e., purification media) were tested as oil pre-columns by adding 1.5 times bed volume of pretreatment material to the column on top of the immobilized lipase. For the control, only enzyme was packed in the column without any pre-column on top. Granular arginine was purchased from Sigma Chemical (St. Louis, Mo.), and used without any further modification for testing the effect of granular arginine. Arginine-coated silica was prepared by dissolving granular arginine in deionized water at 50° C. before adding silica gel (Davisil grade 636 from Aldrich Chemical). After mixing the silica gel-arginine solution for 15 minutes, the liquid was separated from the silica gel by filtering through a medium grade filter paper under reduced pressure. The recovered wet silica gel was dried in a 70° C. oven overnight.

Substrate oil was made up with refined, bleached (RB) soybean oil, which formed the liquid portion of oil in the substrate, and fully hydrogenated soybean oil, which made up the solid fat in the substrate. A substrate blend of RB soybean oil and fully hydrogenated soybean oil (80/20 by weight) was prepared and introduced to the top of the column using a piston pump to feed substrate.

The extent of enzyme reaction was monitored by the change of melting properties of the substrate and products, measured by Mettler Drop Point (MDP) as disclosed in U.S. Application Publication No. 2003/0054509 A1. The substrate blend was pumped to the column at a rate which gave the desired Mettler Drop Point (105-107° F.) of product oil exiting the lipase column, and the pumping rate was adjusted during tests to compensate for loss of lipase activity. FIG. 1 shows the adjustment of the pumping rates for untreated substrate (open circles), substrate treated with granular arginine (closed circles), or substrate treated with arginine-coated silica (closed diamonds).

The results in FIG. 1 are summarized in the Table 1 which shows the half-lives and productivities of lipase exposed to non-treated or arginine treated substrate. The first half-life for each case was determined when the pumping rate was reduced by half of the initial pumping rate. Productivity was determined by dividing the total amounts of the product made during the first half-life by the amount of enzyme (9.4 g).

TABLE 1

Pretreatment Effect of Arginine on TL IM Enzyme Half-Life and Productivity

| Treatment | Half-life (days) | Productivity (g oil/g enzyme) |
|---|---|---|
| Control | 13 | 1220 |
| Granular arginine | 15 | 1451 |
| Arginine-coated silica | 62 | 5000 |

The first half-life of the control was 13 days, giving a productivity of 1220 g oil/g enzyme. This initial activity loss is very typical for immobilized lipases used in this manner. Control did not show the initial protection effect, which the arginine treatments demonstrated. The granular arginine preserved the initial activity of the enzyme for the first 8 days, and then a quick drop after that followed. Half-life and productivity were improved by the granular arginine treatment. Substrate pre-treatment with arginine-coated silica prevented the loss of enzyme activity for the first 20 days before showing a sign of lipase activity decay. The half-life and productivity of pre-treatment with arginine-coated silica is more than four times that of the control.

These experiments show that granular arginine significantly improves the half-life of TL IM lipase. An even greater improvement in the half-life of TL IM lipase is demonstrated when arginine-coated silica gel is used as the purification medium. It is believed that this greater improvement in the half-life is due to the fact that arginine-coated silica has greater surface area than granular arginine.

Example 2

Other amino acids were tested for their ability to increase the half-life of lipase. Preparations of the amino acid coated silica and conditions for column operation were the same as described in Example 1. The extent of enzyme reaction was monitored by the change of melting properties of the substrate and products, measured by Mettler Drop Point (MDP) as disclosed in U.S. Application Publication No. 2003/0054509 A1. The substrate blend was pumped to the column at a rate which gave the desired Mettler Drop Point (105-107°

F.) of product oil exiting the lipase column, and the pumping rate was adjusted during tests to compensate for loss of lipase activity.

FIG. 2 shows the adjustment of the pumping rates for substrate treated with arginine-coated silica (closed diamonds), lysine-coated silica (open circles), histidine-coated silica (closed triangles), and cysteine-coated silica (stars "*"). The data of FIG. 2 is summarized in Table 2.

TABLE 2

Pretreatment Effect of Arginine, Lysine, Histidine or Cysteine on TL IM Enzyme Half-Life and Productivity

| Treatment | Half-life (days) | Productivity (g oil/g enzyme) |
|---|---|---|
| Arginine on silica | 62 | 5000 |
| Lysine on silica | 62 | 5000 |
| Histidine on silica | 50 | 4631 |
| Cysteine on silica | 15 | 1520 |

Significant protective effect was obtained with lysine and histidine on silica. Cysteine provided a small protective effect on lipase half-life (15 days) relative to control (13 days).

Example 3

9.4 g of enzyme (TL IM from Novozymes) was packed in a 1.5 cm diameter jacketed column (30 cm long) at a height of 11.8 cm, which gave 20.8 ml enzyme bed volume. The water circulating through the column jacket was held at 70° C. A substrate blend of soybean oil and fully hydrogenated soybean oil (80/20 by weight) was prepared and introduced to the top of the column using an HPLC pump to feed substrate. The HPLC pump and feed lines were wrapped with heating tape and covered with insulation to prevent any solidification of substrate. The extent of enzyme reaction was monitored by the change of melting properties of the substrate and products, measured as Mettler Drop Point (MDP) as disclosed in U.S. Application Publ. No. 2003/0054509 A1. The substrate blend was pumped to the column at a rate which gave the desired Mettler Drop Point (105-107° F.) of oil exiting the column, and the pumping rate was adjusted during tests to compensate for loss of lipase activity.

Substrate oil was made up in some cases with refined, bleached, deodorized (RBD) soybean oil, which is equivalent to the product of commerce. In some cases substrate oil was made up with oil which had only undergone the refining and bleaching oil (RB). The latter oil forms a preferred substrate from the standpoint of process cost. These oils formed the liquid portion of oil in the substrate given in Table 3.

TABLE 3

Comparative examples. All substrate oils contained 20% fully hydrogenated soybean oil and 80% of the oil indicated in the table.

| Precolumn material | Liquid oil | Lipase half-life (days) | Productivity g oil/g enzyme |
|---|---|---|---|
| None | RB soy | 6 | 462.4 |
| None | RBD soy | 8 | 681.9 |
| None | RBD soy (repeat) | 8 | 798.4 |
| None | RBD soy, column temperature 80° C. | 7 | 423.3 |
| None | RBD soy, column temperature 90° C. | 7 | 618.4 |
| None | RBD soy (freshly redeodorized substrate oil) | 10 | 786.4 |

Enzyme half-life using substrate made with RBD oil averaged 8 days, and was only 6 days using substrate made with RB soy. By redeodorizing the blend of RBD soy and fully hydrogenated soybean oil the half life was extended to 10 days.

Example 4

The tests of Table 4 were conducted as in Example 3 at 70° C., and materials were tested as oil precolumns by adding an equal bed volume of material to the column on top of the immobilized lipase. The extent of enzyme reaction was monitored by the change of melting properties of the substrate and products, measured by Mettler Drop Point (MDP) as disclosed in U.S. Application Publication No. 2003/0054509 A1. The substrate blend was pumped to the column at a rate which gave the desired Mettler Drop Point (105-107° F.) of product oil exiting the lipase column, and the pumping rate was adjusted during tests to compensate for loss of lipase activity.

TABLE 4

| Precolumn material | Liquid oil | Lipase half-life (days) | Productivity g oil/g enzyme |
|---|---|---|---|
| 0.2% Sodium vitride | RB soy | 1 | 103.2 |
| Corn Gluten | RBD soy | 3 | 257.9 |
| Granular Lysine | RBD soy | 5 | 304.9 |
| Sucrose | RBD soy | 5 | 530 |
| Anhydrous sodium citrate | RBD soy | 5 | NA |
| Magnesium silicate | RBD soy | 6 | 398.6 |
| Dextrose | RBD soy | 6 | 490 |
| Rhizopus cell mass | RBD soy | 6 | 469 |
| Used TL IM lipase* | RBD soy | 8 | 798.4 |

*Used TL IM lipase is enzyme which had been used previously in identical interesterification reactions until the activity had been depleted.

Example 5

Ion exchange resins were tested as precolumns (Table 5); otherwise the tests were conducted at 70° C. as in Example 3. To make a redeodorized blend, fully hydrogenated soybean oil was melted into RBD soybean oil and the melted blend was deodorized under standard edible oil refining conditions. The extent of enzyme reaction was monitored by the change of melting properties of the substrate and products, measured by Mettler Drop Point (MDP) as disclosed in U.S. Application Publication No. 2003/0054509 A1. The substrate blend was pumped to the column at a rate which gave the desired Mettler Drop Point (105-107° F.) of product oil exiting the lipase column, and the pumping rate was adjusted during tests to compensate for loss of lipase activity.

TABLE 5

| Precolumn resin | Liquid oil | Lipase half-life (days) | Productivity g oil/g enzyme |
|---|---|---|---|
| EXC04 | RBD soy, redeodorized | 9 | 861.9 |
| Rohm & Haas A-7* | RBD soy | 8 | 825.2 |
| Rohm & Haas A-7, dried** | RBD soy | 16 | 1478.3 |

*The ion exchange resin was dried at 110° C. for 2 hours

**The ion exchange resin was dried in ethanol and ethanol was removed prior to use.

When Rohm & Haas A-7 resin was dried with ethanol prior to use, an increase in the lipase half-life and productivity was noted.

Example 6

Protein-containing materials and an amino acid were tested as precolumns (Table 6); otherwise the tests were conducted at 70° C. as in Example 3. The particular textured vegetable protein used was TVP® brand textured vegetable protein from Archer-Daniels-Midland Company, product code 165 840 (1/16 inch granules), with an as-received moisture content of 6%. The extent of enzyme reaction was monitored by the change of melting properties of the substrate and products, measured by Mettler Drop Point (MDP) as disclosed in U.S. Application Publication No. 2003/0054509 A1. The substrate blend was pumped to the column at a rate which gave the desired Mettler Drop Point (105-107° F.) of product oil exiting the lipase column, and the pumping rate was adjusted during tests to compensate for loss of lipase activity.

TABLE 6

| Precolumn material | Liquid oil | Lipase half-life (days) | Productivity g oil/g enzyme |
|---|---|---|---|
| Arginine | RB soy | 13 | 1242.1 |
| Autoclaved TLIM lipase | RBD soy, redeodorized | 15 | 1119.1 |
| As-received TVP ® brand textured vegetable protein | RB soy with 200 ppm TBHQ, Nitrogen sparge | 16 | 1531.2 |
| TVP ® brand textured vegetable protein oven dried overnight at 70-80° C. | RB soy | 17 | 1587.1 |
| As-received TVP ® brand textured vegetable protein (repeat) | RB soy with 200 ppm TBHQ, Nitrogen sparge | 18 | 1341.8 |
| As-received TVP ® brand textured vegetable protein | RBD soy, redeodorized, covered | >18 | 1644.8 |
| TVP ® brand textured vegetable protein oven-dried overnight at 70-80° C. | RBD soy, redeodorized with 200 ppm TBHQ, Nitrogen sparge | 42 | 3340.1 |

When TVP was dried overnight at 70-80° C. prior to use, an increase in the lipase half-life and productivity was noted.

Example 7

A production scale interesterification reaction was carried out using TVP® brand textured vegetable protein from Archer-Daniels-Midland Company as purification media. A lot of TVP® having product code 165 840 (1/16 inch granules) was dried on a belt dryer at 275° F. during fabrication to a final moisture content of 2%. The dried TVP® was packed into two purification media columns (12-inch diameter and 46-inch height, 87.5 lb TVP® per column). Lipase (Novozyme TL IM, 240 lb) was packed in a heated reactor column (2-ft diameter and 5-ft height).

Feed oil (a blend comprising 80 parts refined, bleached, deodorized soybean oil and 20 parts fully hydrogenated soybean oil) was mixed and heated to 70° C. to ensure full melting of the hydrogenated soybean oil and complete mixing of the feed oil components. The feed oil was pumped through the purification media columns from bottom to top in series before entering the bottom of the heated reactor column at an initial flow rate of about 4 gal/min. Interesterified oil exited the top of the heated reactor column as product. The flow rate of the feed oil was reduced as the enzyme activity slowly decreased to provide product having consistent melt properties. The extent of enzyme reaction was monitored by the change of melting properties of the substrate and products, measured by Mettler Drop Point (MDP) as disclosed in U.S. Application Publication No. 2003/0054509 A1. The substrate blend was pumped to the column at a rate which gave the desired Mettler Drop Point (105-107° F.) of product oil exiting the lipase column, and the pumping rate was adjusted during tests to compensate for loss of lipase activity. The temperature of the heated reactor column was maintained at 70° C.

The lipase produced 994,800 pounds of interesterified oil having satisfactory melt properties (Mettler Drop Point 105-107° F.), so that lipase productivity was 4,145 g oil/g enzyme.

* * *

While the foregoing invention has been described in some detail for purposes of clarity and understanding, it will be appreciated by one skilled in the art from a reading of this disclosure that various changes in form and detail can be made without departing from the true scope of the invention and appended claims. All publications mentioned above are hereby incorporated in their entirety by reference.

What is claimed is:

1. A method for producing refined edible fats or oils comprising:

contacting an initial substrate comprising edible fats or oils with one or more edible textured vegetable proteins in a non-aqueous environment to generate a purified substrate; and contacting the purified substrate with lipase to effect esterification, interesterification or transesterification creating the fats or oils and recovering the fat or oils.

2. The method of claim 1. wherein the textured vegetable protein is a textured soy protein.

3. The method of claim wherein the textured vegetable protein has a moisture content of less than about 5%.

4. The method of claim 3, wherein the moisture content of the textured vegetable protein is from about 2% to about 4%.

5. The method of claim 1, wherein the initial substrate further comprises any of free fatty acids, monohydroxy(alcohols, polyhydroxyl alcohols, esters or combinations thereof.

6. The method of claim 1, the edible fats or oils consisting essentially of any of (i) butterfat, cocoa butter, cocoa butter substitutes, illipe fat, kokum butter, milk fat, mowrah fat, phulwara butter, sal fat, rhea fat, bomeo tallow, lard, lanolin, beef tallow, mutton tallow, tallow, animal fat, canola oil, castor oil, coconut oil, coriander oil, corn oil, cottonseed oil, hazelnut oil, hempseed oil, jatrophy oil, linseed oil, mango kernel oil, meadowfoam oil, mustard oil, neat's foot oil, olive oil, palm oil, palm kernel oil, peanut oil, rapeseed oil, rice bran oil, safflower oil, sasanqus oil, shea butter, soybean oil, sunflower seed oil, tall oil, tsubaki oil, vegetable oils, marine oils which can be converted into plastic fats, marine oils which can be converted into solid fats, menhaden oil, candlefish oil, cod-liver oil, orange roughy oil, pile herd oil, sardine oil, whale oils, herring oils, 1,3-dipaimitoyl-2-monooleine, 1(3)-paimitoyl-3(1)-stearoyl-2monooleine, 1,3-distearoyl-2-monooleine, triglyceride, diglyceride, monoglyceride, behenic acid triglyceride, trioleine, tripalmitine, tristearine, palm olein, palm stearin, palm kernel olein, palm kernel stearin, triglycerides of medium chain fatty acids;

(ii) processed partially hydrogenated oils of (i)

(iii) processed fully hydrogenated oils of (i);

(iv) fractionated oils of (i); or, (v) combinations of any thereof.

7. The method of claim 5, wherein the esters comprise any of wax esters, alkyl esters, methyl esters, ethyl esters, isopropyl esters, octadecyl esters, aryl esters, propylene glycol esters, ethylene glycol esters, 1,2-propanediol esters or 1,3-propanediol esters.

8. The method of claim 1, wherein the initial substrate further comprises one or more fatty acids.

9. The method of claim 1, wherein the textured vegetable protein and the lipase are packed ln one or more columns.

10. The method of claim 1, wherein the purified substrate is prepared by mixing the initial substrate with the textured vegetable protein in a tank for a batch slurry purification reaction or mixing the initial substrate in a series of tanks for a series of batch slurry purification reactions.

11. The method of claim 10, further comprising mixing the purified substrate with the lipase in a tank for a batch slurry reaction, or flowing the purified substrate through a column containing the lipase.

12. The method of claim 1, wherein the lipase is a 1,3-selective lipase.

13. The method of claim 1, wherein the lipase is a non-selective lipase.

14. The method of claim 1, further comprsing:

monitoring enzymatic activity by measuring one or more physical properties of the fats or oils after having contacted the lipase: and adjusting the duration of time for which the purified substrate contacts the lipase, or adjusting the temperature of the initial substrate, the purified substrate, the vegetable protein or the lipase in response to a change in the enzymatic activity to produce fats or oils having a substantially uniform increased proportion of esterification, interesterification, or transesterification relative to the initial substrate.

15. The method of claim 14, further comprising;

adjusting the amount and type of the vegetable protein in response to changes in the physical properties of the fats or oils to increase enzymatic productivity of the lipase.

16. The method of claim 1, wherein the fats or oils produced are 1,3-diglycerides.

17. The method of claim 1, wherein the fats or oils comprise partially hydrogenated soybean oil, partially hydrogenated corn oil, partially hydrogenated cottonseed oil, fully hydrogenated soybean oil, fully hydrogenated corn oil, partially hydrogenated palm oil, partially hydrogenated palm kernel oil, fully hydrogenated palm oil, fully hydrogenated palm kernel oil, fractionated palm oil, fractionated palm kernel oil, fractionated partially hydrogenated palm oil, or fractionated partially hydrogenated palm kernel oil.

18. The method of claim 1, wherein the enzymatic activity half-life of the lipase is more than 2.5 times greater than the enzymatic activity half-life resulting from contacting the lipase with the initial substrate.

19. A method for producing fats or oils comprising:

contacting an initial substrate comprising one or more glycerides with one or more types of edible thermoplastically extruded textured vegetable protein to generate a purified substrate; and contacting the purified substrate with lipase to effect esterification, interesterification or transesterification creating the fats or oils and recovering the fats or oils.

* * * * *